(12) United States Patent
Kaiser et al.

(10) Patent No.: US 7,959,650 B2
(45) Date of Patent: Jun. 14, 2011

(54) ADJUSTABLE KNOTLESS LOOPS

(75) Inventors: Ryan A. Kaiser, Leesburg, IN (US);
 Gregory J. Denham, Warsaw, IN (US);
 Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 278 days.

(21) Appl. No.: 12/196,398

(22) Filed: Aug. 22, 2008

(65) Prior Publication Data

US 2009/0082805 A1 Mar. 26, 2009

Related U.S. Application Data

(63) Continuation-in-part of application No. 11/541,506, filed on Sep. 29, 2006, now Pat. No. 7,601,165, and a continuation-in-part of application No. 11/784,821, filed on Apr. 10, 2007, and a continuation-in-part of application No. 11/935,681, filed on Nov. 6, 2007, now Pat. No. 7,905,903.

(51) Int. Cl.
 *A61B 17/04* (2006.01)
(52) U.S. Cl. ....................................................... 606/232
(58) Field of Classification Search .......... 606/223–225, 606/228, 74, 103; 52/22; 604/103.04; 600/29–30, 600/37; 24/115 H
See application file for complete search history.

(56) References Cited

U.S. PATENT DOCUMENTS

| 26,501 A | 12/1859 | Kendrick et al. |
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A * | 12/1882 | Hughes .......................... 606/203 |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |

(Continued)

FOREIGN PATENT DOCUMENTS

AU 4957264 3/1966

(Continued)

OTHER PUBLICATIONS

"EZ Loc Femoral Fixation Device," copyright 2005 Arthrotek, Inc. (8 sheets).

(Continued)

*Primary Examiner* — Julian W Woo
*Assistant Examiner* — Son Dang
(74) *Attorney, Agent, or Firm* — Harness, Dickey

(57) ABSTRACT

Methods of attaching a soft tissue to an adjacent bone at a defect site are provided. At least one adjustable loop of a flexible construct is passed through the soft tissue. The at least one adjustable loop is passed through a passage construct. A locking member is passed through the at least one adjustable loop and the adjustable loop is reduced about or within the locking member such that the at least one loop is frictionally retained in the passage construct and locked in place by the locking member to thereby secure the soft tissue.

27 Claims, 16 Drawing Sheets

U.S. PATENT DOCUMENTS

| | | |
|---|---|---|
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Himmelstein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |

| | | | | | |
|---|---|---|---|---|---|
| 4,388,921 A | 6/1983 | Sutter et al. | 4,790,297 A | 12/1988 | Luque et al. |
| 4,400,833 A | 8/1983 | Kurland | 4,793,363 A | 12/1988 | Ausherman et al. |
| 4,402,445 A | 9/1983 | Green | 4,809,695 A | 3/1989 | Gwathmey et al. |
| 4,409,974 A | 10/1983 | Freedland | 4,813,406 A | 3/1989 | Ogle, II |
| 4,438,769 A | 3/1984 | Pratt et al. | 4,823,794 A | 4/1989 | Pierce |
| 4,441,489 A | 4/1984 | Evans et al. | 4,828,562 A | 5/1989 | Kenna |
| 4,454,875 A | 6/1984 | Pratt et al. | 4,832,026 A | 5/1989 | Jones |
| 4,462,395 A | 7/1984 | Johnson | 4,834,098 A | 5/1989 | Jones |
| 4,463,753 A | 8/1984 | Gustilo | 4,838,282 A | 6/1989 | Strasser et al. |
| 4,473,102 A | 9/1984 | Ohman et al. | 4,841,960 A | 6/1989 | Garner |
| 4,484,570 A | 11/1984 | Sutter et al. | 4,851,005 A | 7/1989 | Hunt et al. |
| 4,493,323 A | 1/1985 | Albright et al. | 4,858,608 A | 8/1989 | McQuilkin et al. |
| 4,496,468 A | 1/1985 | House et al. | 4,860,513 A | 8/1989 | Whitman |
| 4,505,274 A | 3/1985 | Speelman | 4,863,383 A | 9/1989 | Grafelmann et al. |
| 4,509,516 A | 4/1985 | Richmond | 4,870,957 A | 10/1989 | Goble et al. |
| 4,531,522 A | 7/1985 | Bedi et al. | 4,873,976 A | 10/1989 | Schreiber |
| 4,532,926 A | 8/1985 | O'Holla | 4,887,601 A | 12/1989 | Richards |
| 4,534,350 A | 8/1985 | Golden et al. | 4,890,615 A | 1/1990 | Caspari et al. |
| 4,535,764 A | 8/1985 | Ebert | 4,893,619 A | 1/1990 | Dale et al. |
| 4,537,185 A | 8/1985 | Stednitz | 4,893,974 A | 1/1990 | Fischer et al. |
| 4,549,545 A * | 10/1985 | Levy .................... 606/228 | 4,895,148 A | 1/1990 | Bays et al. |
| 4,549,652 A | 10/1985 | Free | 4,896,668 A | 1/1990 | Popoff et al. |
| 4,561,432 A | 12/1985 | Mazor | 4,898,156 A | 2/1990 | Gatturna et al. |
| 4,564,007 A | 1/1986 | Coombs et al. | 4,899,743 A | 2/1990 | Nicholson et al. |
| 4,570,623 A | 2/1986 | Ellison et al. | 4,901,721 A | 2/1990 | Hakki |
| 4,573,844 A | 3/1986 | Smith | 4,923,461 A | 5/1990 | Caspari et al. |
| 4,576,608 A | 3/1986 | Homsy | 4,927,421 A | 5/1990 | Goble et al. |
| 4,584,722 A | 4/1986 | Levy et al. | 4,946,468 A | 8/1990 | Li |
| 4,590,928 A | 5/1986 | Hunt et al. | 4,950,270 A | 8/1990 | Bowman et al. |
| 4,595,007 A | 6/1986 | Mericle | 4,950,285 A * | 8/1990 | Wilk ..................... 606/232 |
| 4,596,249 A | 6/1986 | Freda et al. | 4,960,381 A | 10/1990 | Niznick |
| 4,602,635 A | 7/1986 | Mulhollan et al. | 4,961,741 A | 10/1990 | Hayhurst |
| 4,602,636 A | 7/1986 | Noiles | 4,968,315 A | 11/1990 | Gatturna |
| 4,604,997 A | 8/1986 | De Bastiani et al. | 4,968,317 A | 11/1990 | Tormala et al. |
| 4,605,414 A | 8/1986 | Czajka | 4,969,886 A | 11/1990 | Cziffer et al. |
| 4,616,650 A | 10/1986 | Green et al. | 4,976,736 A | 12/1990 | White et al. |
| 4,621,640 A | 11/1986 | Mulhollan et al. | 4,978,350 A | 12/1990 | Wagenknecht et al. |
| 4,624,254 A | 11/1986 | McGarry et al. | 4,979,956 A | 12/1990 | Silvestrini |
| 4,632,100 A | 12/1986 | Somers et al. | 4,983,176 A | 1/1991 | Cushman et al. |
| 4,635,637 A | 1/1987 | Schreiber | 4,988,351 A | 1/1991 | Paulos et al. |
| 4,636,121 A | 1/1987 | Miller | 4,994,074 A | 2/1991 | Bezwada et al. |
| 4,641,652 A | 2/1987 | Hutterer et al. | 4,997,433 A | 3/1991 | Goble et al. |
| 4,649,952 A | 3/1987 | Jobe | 5,002,550 A | 3/1991 | Li |
| 4,653,486 A | 3/1987 | Coker | 5,002,562 A | 3/1991 | Oberlander |
| 4,653,487 A | 3/1987 | Maale | 5,007,921 A | 4/1991 | Brown |
| 4,653,489 A | 3/1987 | Tronzo | 5,030,224 A | 7/1991 | Wright et al. |
| 4,655,777 A | 4/1987 | Dunn et al. | 5,037,422 A | 8/1991 | Hayhurst et al. |
| 4,662,068 A | 5/1987 | Polonsky | 5,041,129 A | 8/1991 | Hayhurst et al. |
| 4,667,662 A | 5/1987 | Titone et al. | 5,046,513 A | 9/1991 | Gatturna et al. |
| 4,667,675 A | 5/1987 | Davis | 5,047,030 A | 9/1991 | Draenert et al. |
| 4,669,473 A | 6/1987 | Richards et al. | 5,053,046 A | 10/1991 | Janese |
| 4,683,895 A | 8/1987 | Pohndorf | 5,053,047 A | 10/1991 | Yoon |
| 4,688,561 A | 8/1987 | Reese | 5,059,201 A | 10/1991 | Asnis |
| 4,690,169 A | 9/1987 | Jobe | 5,059,206 A | 10/1991 | Winters |
| 4,705,040 A | 11/1987 | Mueller et al. | 5,062,344 A * | 11/1991 | Gerker ..................... 87/8 |
| 4,708,132 A | 11/1987 | Silvestrini | 5,062,843 A | 11/1991 | Mahony, III |
| 4,716,893 A | 1/1988 | Fischer et al. | 5,074,874 A * | 12/1991 | Yoon et al. ............. 606/224 |
| 4,719,671 A | 1/1988 | Ito et al. | 5,078,731 A | 1/1992 | Hayhurst |
| 4,719,917 A | 1/1988 | Barrows et al. | 5,078,843 A | 1/1992 | Pratt |
| 4,723,540 A | 2/1988 | Gilmer, Jr. | 5,084,050 A | 1/1992 | Draenert et al. |
| 4,724,839 A | 2/1988 | Bedi et al. | 5,084,058 A | 1/1992 | Li |
| 4,728,332 A | 3/1988 | Albrektsson et al. | 5,085,661 A | 2/1992 | Moss |
| 4,738,255 A | 4/1988 | Goble et al. | 5,087,263 A | 2/1992 | Li |
| 4,741,330 A | 5/1988 | Hayhurst | 5,092,866 A | 3/1992 | Breard et al. |
| 4,741,336 A | 5/1988 | Failla et al. | 5,098,435 A | 3/1992 | Stednitz et al. |
| 4,744,353 A | 5/1988 | McFarland | 5,100,415 A | 3/1992 | Hayhurst |
| 4,744,793 A | 5/1988 | Parr et al. | 5,100,417 A | 3/1992 | Cerier et al. |
| 4,750,492 A | 6/1988 | Jacobs | 5,116,337 A | 5/1992 | Johnson |
| 4,760,843 A | 8/1988 | Fischer et al. | 5,116,373 A | 5/1992 | Jakob et al. |
| 4,760,844 A | 8/1988 | Kyle | 5,116,375 A | 5/1992 | Hofmann |
| 4,760,848 A | 8/1988 | Hasson | 5,123,913 A * | 6/1992 | Wilk et al. ............. 606/232 |
| 4,772,261 A | 9/1988 | Von Hoff et al. | 5,127,785 A | 7/1992 | Faucher et al. |
| 4,772,286 A | 9/1988 | Goble et al. | 5,129,901 A | 7/1992 | Decoste |
| 4,773,910 A | 9/1988 | Chen et al. | 5,129,902 A | 7/1992 | Goble et al. |
| 4,775,380 A | 10/1988 | Seedhom et al. | 5,129,904 A | 7/1992 | Illi et al. |
| 4,776,328 A | 10/1988 | Frey et al. | 5,129,906 A | 7/1992 | Ross et al. |
| 4,781,190 A | 11/1988 | Lee et al. | 5,139,499 A | 8/1992 | Small et al. |
| 4,784,126 A | 11/1988 | Hourahane et al. | 5,139,520 A | 8/1992 | Rosenberg |
| 4,787,882 A | 11/1988 | Claren et al. | 5,143,498 A | 9/1992 | Whitman |

| Patent No. | Date | Name |
|---|---|---|
| 5,147,362 A | 9/1992 | Goble |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A * | 6/1993 | Yoon ........................ 606/223 |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,258,015 A | 11/1993 | Li et al. |
| 5,258,016 A | 11/1993 | DiPoto et al. |
| 5,258,040 A | 11/1993 | Bruchman et al. |
| 5,268,001 A | 12/1993 | Nicholson et al. |
| 5,269,160 A | 12/1993 | Wood |
| 5,269,783 A | 12/1993 | Sander |
| 5,269,809 A | 12/1993 | Hayhurst et al. |
| 5,281,422 A | 1/1994 | Badylak et al. |
| 5,282,809 A | 2/1994 | Kammerer et al. |
| 5,282,832 A | 2/1994 | Toso et al. |
| 5,285,040 A | 2/1994 | Brandberg et al. |
| 5,290,217 A | 3/1994 | Campos |
| 5,306,301 A | 4/1994 | Graf et al. |
| 5,312,422 A | 5/1994 | Trott |
| 5,312,438 A | 5/1994 | Johnson |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,342,369 A | 8/1994 | Harryman, II |
| 5,346,462 A | 9/1994 | Barber |
| 5,354,298 A | 10/1994 | Lee et al. |
| 5,356,413 A | 10/1994 | Martins et al. |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A * | 1/1995 | Totakura et al. ............ 606/228 |
| 5,391,171 A | 2/1995 | Schmieding |
| 5,391,176 A | 2/1995 | de la Torre |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,417,691 A | 5/1995 | Hayhurst |
| 5,417,712 A | 5/1995 | Whittaker et al. |
| 5,423,819 A | 6/1995 | Small et al. |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,439,684 A | 8/1995 | Prewett et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,451,203 A | 9/1995 | Lamb |
| 5,454,811 A | 10/1995 | Huebner |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,736 A | 4/1996 | Reimels et al. |
| 5,507,754 A | 4/1996 | Green et al. |
| 5,520,691 A | 5/1996 | Branch |
| 5,520,702 A | 5/1996 | Sauer et al. |
| 5,522,817 A | 6/1996 | Sander et al. |
| 5,522,820 A | 6/1996 | Caspari et al. |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,534,012 A | 7/1996 | Bonutti |
| 5,540,718 A | 7/1996 | Bartlett |
| 5,545,178 A | 8/1996 | Kensey et al. |
| 5,545,228 A | 8/1996 | Kambin |
| 5,549,613 A | 8/1996 | Goble et al. |
| 5,549,617 A | 8/1996 | Green et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |

| Patent No. | Date | Name |
|---|---|---|
| 5,573,548 A | 11/1996 | Nazre et al. |
| 5,577,299 A * | 11/1996 | Thompson et al. ......... 24/131 C |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,295 A * | 7/1997 | Yoon ............................. 606/151 |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,352 A | 10/1997 | Clancy, III et al. |
| 5,683,419 A | 11/1997 | Thal |
| 5,688,285 A | 11/1997 | Yamada et al. |
| 5,690,676 A | 11/1997 | DiPoto et al. |
| 5,690,678 A | 11/1997 | Johnson |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,718,717 A | 2/1998 | Bonutti |
| 5,720,747 A * | 2/1998 | Burke ............................. 606/74 |
| 5,720,765 A | 2/1998 | Thal |
| 5,720,766 A | 2/1998 | Zang et al. |
| 5,725,549 A | 3/1998 | Lam |
| 5,725,556 A | 3/1998 | Moser et al. |
| 5,725,581 A | 3/1998 | Brånemark et al. |
| 5,725,582 A * | 3/1998 | Bevan et al. ................... 606/263 |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,766,176 A | 6/1998 | Duncan |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,928 A | 8/1998 | Kogasaka et al. |
| 5,800,407 A | 9/1998 | Eldor et al. |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,860,973 A | 1/1999 | Michelson |
| 5,868,740 A | 2/1999 | LeVeen et al. |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,267 A | 7/1999 | Bonutti et al. |
| 5,931,838 A | 8/1999 | Vito |
| 5,931,844 A | 8/1999 | Thompson et al. |
| 5,931,869 A | 8/1999 | Boucher et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,783 A | 10/1999 | Grafton et al. |
| 5,968,045 A | 10/1999 | Frazier |

| | | | | | | |
|---|---|---|---|---|---|---|
| 5,968,047 | A | 10/1999 | Reed | 6,206,883 | B1 | 3/2001 | Tunc |
| 5,976,125 | A | 11/1999 | Graham | 6,210,376 | B1 | 4/2001 | Grayson |
| 5,976,127 | A | 11/1999 | Lax | 6,214,012 | B1 | 4/2001 | Karpman et al. |
| 5,980,524 | A | 11/1999 | Justin et al. | 6,221,107 | B1 | 4/2001 | Steiner et al. |
| 5,980,558 | A | 11/1999 | Wiley | 6,228,096 | B1 | 5/2001 | Marchand |
| 5,980,559 | A | 11/1999 | Bonutti | 6,231,592 | B1 | 5/2001 | Bonutti et al. |
| 5,989,252 | A | 11/1999 | Fumex et al. | 6,235,057 | B1 | 5/2001 | Roger et al. |
| 5,989,256 | A | 11/1999 | Kuslich et al. | 6,238,395 | B1 | 5/2001 | Bonutti |
| 5,989,282 | A | 11/1999 | Bonutti | 6,241,734 | B1 | 6/2001 | Scribner et al. |
| 5,993,452 | A | 11/1999 | Vandewalle | 6,241,747 | B1 | 6/2001 | Ruff |
| 5,997,542 | A | 12/1999 | Burke | 6,241,771 | B1 | 6/2001 | Gresser et al. |
| 5,997,552 | A | 12/1999 | Person et al. | 6,245,081 | B1 | 6/2001 | Bowman et al. |
| 6,001,100 | A | 12/1999 | Sherman et al. | 6,258,091 | B1 | 7/2001 | Sevrain et al. |
| 6,007,567 | A | 12/1999 | Bonutti | 6,267,766 | B1 | 7/2001 | Burkhart |
| 6,010,525 | A | 1/2000 | Bonutti et al. | 6,269,716 | B1 | 8/2001 | Amis |
| 6,016,727 | A | 1/2000 | Morgan | 6,270,518 | B1 | 8/2001 | Pedlick et al. |
| 6,022,352 | A | 2/2000 | Vandewalle | 6,273,890 | B1 | 8/2001 | Frazier |
| 6,022,373 | A | 2/2000 | Li | 6,283,973 | B1 | 9/2001 | Hubbard et al. |
| 6,024,758 | A | 2/2000 | Thal | 6,283,996 | B1 | 9/2001 | Chervitz et al. |
| 6,027,523 | A | 2/2000 | Schmieding | 6,287,325 | B1 | 9/2001 | Bonutti |
| 6,033,430 | A | 3/2000 | Bonutti | 6,293,961 | B2 | 9/2001 | Schwartz et al. |
| 6,039,753 | A | 3/2000 | Meislin | 6,296,659 | B1 | 10/2001 | Foerster |
| 6,042,601 | A | 3/2000 | Smith | 6,299,615 | B1 | 10/2001 | Huebner |
| 6,045,551 | A | 4/2000 | Bonutti | 6,302,888 | B1 | 10/2001 | Mellinger et al. |
| 6,045,571 | A | 4/2000 | Hill et al. | 6,306,156 | B1 | 10/2001 | Clark |
| 6,045,573 | A | 4/2000 | Wenstrom, Jr. et al. | 6,306,159 | B1 | 10/2001 | Schwartz et al. |
| 6,045,574 | A | 4/2000 | Thal | 6,309,405 | B1 | 10/2001 | Bonutti |
| 6,047,826 | A | 4/2000 | Kalinski et al. | 6,312,448 | B1 | 11/2001 | Bonutti |
| 6,048,343 | A | 4/2000 | Mathis et al. | 6,319,271 | B1 | 11/2001 | Schwartz et al. |
| 6,051,006 | A | 4/2000 | Shluzas et al. | 6,328,758 | B1 | 12/2001 | Tornier et al. |
| 6,053,916 | A | 4/2000 | Moore | 6,342,060 | B1 | 1/2002 | Adams |
| 6,056,752 | A | 5/2000 | Roger et al. | 6,343,531 | B2 | 2/2002 | Amis |
| 6,056,772 | A | 5/2000 | Bonutti | 6,364,897 | B1 | 4/2002 | Bonutti |
| 6,056,773 | A | 5/2000 | Bonutti | 6,368,322 | B1 | 4/2002 | Luks et al. |
| 6,059,817 | A | 5/2000 | Bonutti et al. | 6,368,326 | B1 | 4/2002 | Dakin et al. |
| 6,062,344 | A | 5/2000 | Okabe et al. | 6,368,343 | B1 | 4/2002 | Bonutti et al. |
| 6,068,648 | A | 5/2000 | Cole et al. | 6,371,124 | B1 | 4/2002 | Whelan |
| 6,074,403 | A | 6/2000 | Nord | 6,379,361 | B1 | 4/2002 | Beck, Jr. et al. |
| 6,077,277 | A | 6/2000 | Mollenauer et al. | 6,383,190 | B1 | 5/2002 | Preissman |
| 6,077,292 | A | 6/2000 | Bonutti | 6,383,199 | B2 | 5/2002 | Carter et al. |
| 6,086,591 | A | 7/2000 | Bojarski | 6,387,113 | B1 | 5/2002 | Hawkins et al. |
| 6,086,592 | A | 7/2000 | Rosenberg et al. | 6,387,129 | B2 | 5/2002 | Rieser et al. |
| 6,086,608 | A | 7/2000 | Ek et al. | 6,398,785 | B2 | 6/2002 | Carchidi et al. |
| 6,096,060 | A | 8/2000 | Fitts et al. | 6,406,479 | B1 | 6/2002 | Justin et al. |
| 6,099,530 | A | 8/2000 | Simonian et al. | 6,409,743 | B1 | 6/2002 | Fenton, Jr. |
| 6,099,568 | A | 8/2000 | Simonian et al. | 6,413,260 | B1 | 7/2002 | Berrevoets et al. |
| 6,106,545 | A | 8/2000 | Egan | 6,423,088 | B1 | 7/2002 | Fenton, Jr. |
| 6,110,128 | A | 8/2000 | Andelin et al. | 6,428,562 | B2 | 8/2002 | Bonutti |
| 6,117,160 | A | 9/2000 | Bonutti | 6,432,123 | B2 | 8/2002 | Schwartz et al. |
| 6,117,162 | A | 9/2000 | Schmieding et al. | 6,436,124 | B1 | 8/2002 | Anderson et al. |
| 6,123,710 | A | 9/2000 | Pinczewski et al. | 6,440,134 | B1 | 8/2002 | Zaccherotti et al. |
| 6,132,433 | A | 10/2000 | Whelan | 6,440,136 | B1 | 8/2002 | Gambale et al. |
| 6,132,437 | A | 10/2000 | Omurtag et al. | 6,447,516 | B1 | 9/2002 | Bonutti |
| 6,139,565 | A | 10/2000 | Stone et al. | 6,451,030 | B2 | 9/2002 | Li et al. |
| RE36,974 | E | 11/2000 | Bonutti | 6,454,768 | B1 | 9/2002 | Jackson |
| 6,143,017 | A | 11/2000 | Thal | 6,458,134 | B1 | 10/2002 | Songer et al. |
| 6,146,406 | A | 11/2000 | Shluzas et al. | 6,461,373 | B2 | 10/2002 | Wyman et al. |
| 6,146,408 | A | 11/2000 | Bartlett | 6,464,713 | B2 | 10/2002 | Bonutti |
| 6,149,653 | A | 11/2000 | Deslauriers | 6,468,293 | B2 | 10/2002 | Bonutti et al. |
| 6,149,669 | A | 11/2000 | Li | 6,471,707 | B1 | 10/2002 | Miller et al. |
| 6,152,928 | A | 11/2000 | Wenstrom, Jr. | 6,475,230 | B1 | 11/2002 | Bonutti et al. |
| 6,152,934 | A | 11/2000 | Harper et al. | 6,482,210 | B1 | 11/2002 | Skiba et al. |
| 6,152,936 | A | 11/2000 | Christy et al. | 6,485,504 | B1 | 11/2002 | Johnson et al. |
| 6,152,949 | A | 11/2000 | Bonutti | 6,497,901 | B1 | 12/2002 | Royer |
| 6,156,039 | A | 12/2000 | Thal | 6,500,184 | B1 | 12/2002 | Chan et al. |
| 6,156,056 | A | 12/2000 | Kearns et al. | 6,500,195 | B2 | 12/2002 | Bonutti |
| 6,159,234 | A | 12/2000 | Bonutti et al. | RE37,963 | E | 1/2003 | Thal |
| 6,165,203 | A | 12/2000 | Krebs | 6,503,267 | B2 | 1/2003 | Bonutti et al. |
| 6,168,598 | B1 | 1/2001 | Martello | 6,508,820 | B2 | 1/2003 | Bales |
| 6,168,628 | B1 | 1/2001 | Huebner | 6,508,821 | B1 | 1/2003 | Schwartz et al. |
| 6,179,840 | B1 | 1/2001 | Bowman | 6,508,830 | B2 | 1/2003 | Steiner |
| 6,187,025 | B1 | 2/2001 | Machek | 6,511,498 | B1 * | 1/2003 | Fumex ............ 606/232 |
| 6,190,401 | B1 | 2/2001 | Green et al. | 6,511,499 | B2 | 1/2003 | Schmieding et al. |
| 6,190,411 | B1 | 2/2001 | Lo et al. | 6,517,542 | B1 | 2/2003 | Papay et al. |
| 6,193,754 | B1 | 2/2001 | Seedhom et al. | 6,517,552 | B1 | 2/2003 | Nord et al. |
| 6,200,329 | B1 | 3/2001 | Fung et al. | 6,517,578 | B2 | 2/2003 | Hein et al. |
| 6,200,330 | B1 | 3/2001 | Benderev et al. | 6,517,579 | B1 | 2/2003 | Paulos et al. |
| 6,203,565 | B1 | 3/2001 | Bonutti et al. | 6,520,964 | B2 | 2/2003 | Tallarida et al. |
| 6,203,572 | B1 | 3/2001 | Johnson et al. | 6,520,980 | B1 | 2/2003 | Foerster |

| Patent | Type | Date | Inventor |
|---|---|---|---|
| 6,524,317 | B1 | 2/2003 | Ritchart et al. |
| 6,527,777 | B2 | 3/2003 | Justin |
| 6,527,794 | B1 | 3/2003 | McDevitt et al. |
| 6,527,795 | B1 | 3/2003 | Lizardi |
| 6,533,795 | B1 | 3/2003 | Tran et al. |
| 6,533,802 | B2 | 3/2003 | Bojarski et al. |
| 6,537,319 | B2 | 3/2003 | Whelan |
| 6,540,750 | B2 | 4/2003 | Burkhart |
| 6,540,770 | B1 | 4/2003 | Tornier et al. |
| 6,544,281 | B2 | 4/2003 | ElAttrache et al. |
| 6,547,564 | B1 | 4/2003 | Hansson et al. |
| 6,547,800 | B2 | 4/2003 | Foerster et al. |
| 6,551,330 | B1 | 4/2003 | Bain et al. |
| 6,551,343 | B1 | 4/2003 | Tormala et al. |
| 6,553,802 | B1 | 4/2003 | Jacob et al. |
| 6,554,830 | B1 | 4/2003 | Chappius |
| 6,554,852 | B1 | 4/2003 | Oberlander |
| 6,554,862 | B2 | 4/2003 | Hays et al. |
| 6,562,071 | B2 | 5/2003 | Jarvinen et al. |
| 6,565,572 | B2 | 5/2003 | Chappius |
| 6,565,573 | B2 | 5/2003 | Ferrante et al. |
| 6,569,186 | B1 | 5/2003 | Winters et al. |
| 6,569,187 | B1 | 5/2003 | Bonutti et al. |
| 6,572,635 | B1 | 6/2003 | Bonutti |
| 6,575,925 | B1 | 6/2003 | Noble |
| 6,579,295 | B1 | 6/2003 | Supinski |
| 6,582,453 | B1 | 6/2003 | Tran et al. |
| 6,585,730 | B1 | 7/2003 | Foerster |
| 6,585,740 | B2 | 7/2003 | Schlapfer et al. |
| 6,585,750 | B2 | 7/2003 | Bonutti et al. |
| 6,589,245 | B1 | 7/2003 | Weiler et al. |
| 6,589,246 | B1 | 7/2003 | Hack et al. |
| 6,592,609 | B1 | 7/2003 | Bonutti |
| 6,595,911 | B2 | 7/2003 | LoVuolo |
| 6,599,289 | B1 | 7/2003 | Bojarski et al. |
| 6,605,096 | B1 | 8/2003 | Ritchart |
| 6,607,548 | B2 | 8/2003 | Pohjonen et al. |
| 6,610,079 | B1 | 8/2003 | Li et al. |
| 6,613,018 | B2 | 9/2003 | Bagga et al. |
| 6,616,694 | B1 | 9/2003 | Hart |
| 6,620,166 | B1 | 9/2003 | Wenstrom, Jr. et al. |
| 6,620,185 | B1 | 9/2003 | Harvie et al. |
| 6,620,195 | B2 | 9/2003 | Goble et al. |
| 6,620,329 | B2 | 9/2003 | Rosen et al. |
| 6,620,349 | B1 | 9/2003 | Lopez |
| 6,623,492 | B1 | 9/2003 | Berube et al. |
| 6,623,524 | B2 | 9/2003 | Schmieding |
| 6,626,910 | B1 | 9/2003 | Hugues et al. |
| 6,626,919 | B1 | 9/2003 | Swanstrom |
| 6,629,977 | B1 | 10/2003 | Wolf |
| 6,635,073 | B2 | 10/2003 | Bonutti |
| 6,638,279 | B2 | 10/2003 | Bonutti |
| 6,641,596 | B1 | 11/2003 | Lizardi |
| 6,641,597 | B2 | 11/2003 | Burkhart et al. |
| 6,645,227 | B2 | 11/2003 | Fallin et al. |
| 6,652,562 | B2 | 11/2003 | Collier et al. |
| 6,652,563 | B2 | 11/2003 | Dreyfuss |
| 6,656,182 | B1 | 12/2003 | Hayhurst |
| 6,656,183 | B2 | 12/2003 | Colleran et al. |
| 6,658,182 | B1 | 12/2003 | Gonthier et al. |
| 6,660,008 | B1 | 12/2003 | Foerster et al. |
| 6,660,022 | B1 | 12/2003 | Li et al. |
| 6,663,634 | B2 | 12/2003 | Ahrens et al. |
| 6,663,656 | B2 | 12/2003 | Schmieding et al. |
| 6,666,868 | B2 | 12/2003 | Fallin |
| 6,682,549 | B2 | 1/2004 | Bartlett |
| 6,685,728 | B2 | 2/2004 | Sinnott et al. |
| 6,689,137 | B2 | 2/2004 | Reed |
| 6,689,154 | B2 | 2/2004 | Bartlett |
| 6,692,499 | B2 | 2/2004 | Tormala et al. |
| 6,712,849 | B2 | 3/2004 | Re et al. |
| 6,716,224 | B2 | 4/2004 | Singhatat |
| 6,716,957 | B2 | 4/2004 | Tunc |
| 6,730,092 | B2 | 5/2004 | Songer |
| 6,730,124 | B2 | 5/2004 | Steiner |
| 6,736,799 | B1 | 5/2004 | Erbe et al. |
| 6,746,483 | B1 | 6/2004 | Bojarski et al. |
| 6,755,836 | B1 | 6/2004 | Lewis |
| 6,761,739 | B2 | 7/2004 | Shepard |
| 6,767,037 | B2 | 7/2004 | Wenstrom, Jr. |
| 6,770,076 | B2 | 8/2004 | Foerster |
| 6,770,084 | B1 | 8/2004 | Bain et al. |
| 6,773,450 | B2 | 8/2004 | Leung et al. |
| 6,780,190 | B2 | 8/2004 | Maroney |
| 6,780,198 | B1 | 8/2004 | Gregoire et al. |
| 6,802,862 | B1 | 10/2004 | Roger et al. |
| 6,808,502 | B2 | 10/2004 | Nguyen et al. |
| 6,808,526 | B1 | 10/2004 | Magerl et al. |
| 6,814,741 | B2 | 11/2004 | Bowman et al. |
| 6,830,572 | B2 | 12/2004 | McDevitt et al. |
| 6,833,005 | B1 | 12/2004 | Mantas et al. |
| 6,840,953 | B2 | 1/2005 | Martinek |
| 6,860,885 | B2 | 3/2005 | Bonutti |
| 6,863,671 | B1 | 3/2005 | Strobel et al. |
| 6,872,040 | B2 | 3/2005 | Deeg et al. |
| 6,875,216 | B2 | 4/2005 | Wolf |
| 6,884,249 | B2 | 4/2005 | May et al. |
| 6,887,259 | B2 | 5/2005 | Lizardi |
| 6,890,354 | B2 | 5/2005 | Steiner et al. |
| 6,893,448 | B2 | 5/2005 | O'Quinn et al. |
| 6,896,686 | B2 | 5/2005 | Weber |
| 6,899,722 | B2 | 5/2005 | Bonutti |
| 6,902,573 | B2 | 6/2005 | Strobel et al. |
| 6,908,466 | B1 | 6/2005 | Bonutti et al. |
| 6,916,292 | B2 | 7/2005 | Morawski et al. |
| 6,916,321 | B2 | 7/2005 | TenHuisen et al. |
| 6,921,402 | B2 | 7/2005 | Contiliano et al. |
| 6,923,823 | B1 | 8/2005 | Bartlett et al. |
| 6,923,824 | B2 | 8/2005 | Morgan et al. |
| 6,951,565 | B2 | 10/2005 | Keane et al. |
| 6,972,027 | B2 | 12/2005 | Fallin et al. |
| 6,980,903 | B2 | 12/2005 | Daniels et al. |
| 6,986,781 | B2 | 1/2006 | Smith |
| 6,989,034 | B2 | 1/2006 | Hammer et al. |
| 7,066,942 | B2 | 6/2006 | Treace |
| 7,066,944 | B2 | 6/2006 | Laufer et al. |
| 7,105,010 | B2 | 9/2006 | Hart et al. |
| 7,112,221 | B2 | 9/2006 | Harris et al. |
| 7,118,583 | B2 | 10/2006 | O'Quinn et al. |
| 7,137,996 | B2 | 11/2006 | Steiner et al. |
| 7,141,066 | B2 | 11/2006 | Steiner et al. |
| 7,153,307 | B2 | 12/2006 | Scribner et al. |
| 7,153,312 | B1 | 12/2006 | Torrie et al. |
| 7,201,722 | B2 | 4/2007 | Krueger |
| 7,255,675 | B2 | 8/2007 | Gertner et al. |
| 7,261,716 | B2 | 8/2007 | Strobel et al. |
| 7,264,634 | B2 | 9/2007 | Schmieding |
| 7,285,124 | B2 | 10/2007 | Foerster |
| 7,306,417 | B2 | 12/2007 | Dorstewitz |
| 7,326,222 | B2 | 2/2008 | Dreyfuss et al. |
| 7,390,332 | B2 | 6/2008 | Selvitelli et al. |
| 7,601,165 | B2 | 10/2009 | Stone |
| 7,608,098 | B1 | 10/2009 | Stone et al. |
| 7,615,076 | B2 | 11/2009 | Cauthen, III et al. |
| 7,632,287 | B2 | 12/2009 | Baker et al. |
| 7,651,509 | B2 | 1/2010 | Bojarski et al. |
| 7,658,751 | B2 | 2/2010 | Stone et al. |
| 7,670,279 | B2 | 3/2010 | Gertner |
| 7,678,123 | B2 | 3/2010 | Chanduszko |
| 7,695,493 | B2 | 4/2010 | Saadat et al. |
| 7,736,379 | B2 | 6/2010 | Ewers et al. |
| 7,758,594 | B2 | 7/2010 | Lamson et al. |
| 7,819,895 | B2 | 10/2010 | Ginn et al. |
| 7,875,058 | B2 | 1/2011 | Holmes, Jr. |
| 2001/0014825 | A1 | 8/2001 | Burke et al. |
| 2001/0037131 | A1 | 11/2001 | Schmieding et al. |
| 2001/0037153 | A1 | 11/2001 | Rockwood et al. |
| 2001/0041916 | A1 | 11/2001 | Bonutti |
| 2001/0041937 | A1 | 11/2001 | Rieser et al. |
| 2001/0041938 | A1 | 11/2001 | Hein |
| 2001/0044639 | A1 | 11/2001 | Levinson |
| 2001/0047206 | A1 | 11/2001 | Sklar et al. |
| 2001/0051816 | A1 | 12/2001 | Enzerink et al. |
| 2001/0053934 | A1 | 12/2001 | Schmieding |
| 2002/0001964 | A1 | 1/2002 | Choi |
| 2002/0004669 | A1 | 1/2002 | Bartlett |
| 2002/0007182 | A1 | 1/2002 | Kim |
| 2002/0010513 | A1 | 1/2002 | Schmieding |

| | | | | | | |
|---|---|---|---|---|---|---|
| 2002/0013608 A1 | 1/2002 | ElAttrache et al. | | 2004/0267277 A1 | 12/2004 | Zannis et al. |
| 2002/0019649 A1 | 2/2002 | Sikora et al. | | 2004/0267304 A1 | 12/2004 | Zannis et al. |
| 2002/0055780 A1 | 5/2002 | Sklar | | 2005/0027307 A1 | 2/2005 | Schwartz et al. |
| 2002/0058966 A1 | 5/2002 | Tormala et al. | | 2005/0033363 A1 | 2/2005 | Bojarski et al. |
| 2002/0099411 A1 | 7/2002 | Bartlett | | 2005/0038426 A1 | 2/2005 | Chan |
| 2002/0111653 A1 | 8/2002 | Foerster | | 2005/0055027 A1 | 3/2005 | Yeung et al. |
| 2002/0120270 A1 | 8/2002 | Trieu et al. | | 2005/0064042 A1 | 3/2005 | Vunjak-Novakovic et al. |
| 2002/0120292 A1 | 8/2002 | Morgan | | 2005/0074495 A1 | 4/2005 | Schwartz et al. |
| 2002/0123752 A1 | 9/2002 | Schultheiss et al. | | 2005/0090828 A1 | 4/2005 | Alford |
| 2002/0128684 A1 | 9/2002 | Foerster | | 2005/0096696 A1 | 5/2005 | Forsberg |
| 2002/0147463 A1 | 10/2002 | Martinek | | 2005/0096697 A1 | 5/2005 | Forsberg et al. |
| 2002/0161401 A1 | 10/2002 | Steiner | | 2005/0107828 A1 | 5/2005 | Reese |
| 2002/0161439 A1 | 10/2002 | Strobel et al. | | 2005/0119531 A1 | 6/2005 | Sharratt |
| 2002/0169452 A1 | 11/2002 | Tormala et al. | | 2005/0125073 A1 | 6/2005 | Orban et al. |
| 2002/0169477 A1 | 11/2002 | Demopulos et al. | | 2005/0137600 A1 | 6/2005 | Jacobs et al. |
| 2002/0169478 A1 | 11/2002 | Schwartz et al. | | 2005/0149033 A1 | 7/2005 | McGuire et al. |
| 2002/0173788 A1 | 11/2002 | Bojarski et al. | | 2005/0159812 A1 | 7/2005 | Dinger et al. |
| 2002/0188298 A1 | 12/2002 | Chan | | 2005/0165416 A1 | 7/2005 | Bojarski et al. |
| 2003/0023268 A1 | 1/2003 | Lizardi | | 2005/0165482 A1 | 7/2005 | Goldhahn et al. |
| 2003/0032961 A1 | 2/2003 | Pelo et al. | | 2005/0187565 A1 | 8/2005 | Baker et al. |
| 2003/0033021 A1 | 2/2003 | Plouhar et al. | | 2005/0203620 A1 | 9/2005 | Steiner et al. |
| 2003/0033022 A1 | 2/2003 | Plouhar et al. | | 2005/0222618 A1 | 10/2005 | Dreyfuss et al. |
| 2003/0036797 A1 | 2/2003 | Malaviya et al. | | 2005/0222619 A1 | 10/2005 | Dreyfuss et al. |
| 2003/0036801 A1 | 2/2003 | Schwartz et al. | | 2005/0228448 A1 | 10/2005 | Li |
| 2003/0065391 A1 | 4/2003 | Re et al. | | 2005/0267479 A1 | 12/2005 | Morgan et al. |
| 2003/0078603 A1 | 4/2003 | Schaller et al. | | 2005/0267533 A1 | 12/2005 | Gertner |
| 2003/0078617 A1 | 4/2003 | Schwartz et al. | | 2005/0277961 A1 | 12/2005 | Stone et al. |
| 2003/0083662 A1 | 5/2003 | Middleton | | 2005/0283040 A1 | 12/2005 | Greenhalgh |
| 2003/0088251 A1 | 5/2003 | Braun et al. | | 2005/0283156 A1 | 12/2005 | Schmieding et al. |
| 2003/0088272 A1 | 5/2003 | Smith | | 2005/0283158 A1 | 12/2005 | West |
| 2003/0105477 A1 | 6/2003 | Schwartz et al. | | 2005/0283192 A1 | 12/2005 | Torrie et al. |
| 2003/0120309 A1 | 6/2003 | Colleran et al. | | 2006/0030884 A1 | 2/2006 | Yeung et al. |
| 2003/0130694 A1 | 7/2003 | Bojarski et al. | | 2006/0030948 A1 | 2/2006 | Manrique et al. |
| 2003/0135214 A1 | 7/2003 | Fetto et al. | | 2006/0036265 A1 | 2/2006 | Dant |
| 2003/0135239 A1 | 7/2003 | Gabriel et al. | | 2006/0064126 A1 | 3/2006 | Fallin et al. |
| 2003/0135963 A1 | 7/2003 | Holbrook et al. | | 2006/0069334 A1 | 3/2006 | Moskowitz |
| 2003/0152522 A1 | 8/2003 | Miller et al. | | 2006/0084943 A1 | 4/2006 | Rosenman et al. |
| 2003/0167072 A1 | 9/2003 | Oberlander | | 2006/0100627 A1 | 5/2006 | Stone et al. |
| 2003/0167090 A1 | 9/2003 | Chervitz et al. | | 2006/0121084 A1 | 6/2006 | Borden et al. |
| 2003/0171811 A1 | 9/2003 | Steiner et al. | | 2006/0135958 A1 | 6/2006 | Marissen et al. |
| 2003/0176865 A1 | 9/2003 | Supinski | | 2006/0167481 A1 | 7/2006 | Baker et al. |
| 2003/0176919 A1 | 9/2003 | Schmieding | | 2006/0167482 A1 | 7/2006 | Swain et al. |
| 2003/0181925 A1 | 9/2003 | Bain et al. | | 2006/0178680 A1 | 8/2006 | Nelson et al. |
| 2003/0195528 A1 | 10/2003 | Ritchart | | 2006/0189993 A1 | 8/2006 | Stone |
| 2003/0208210 A1 | 11/2003 | Dreyfuss et al. | | 2006/0190042 A1 | 8/2006 | Stone et al. |
| 2003/0220660 A1 | 11/2003 | Kortenbach et al. | | 2006/0229671 A1 | 10/2006 | Steiner et al. |
| 2003/0225459 A1 | 12/2003 | Hammer et al. | | 2006/0247642 A1 | 11/2006 | Stone et al. |
| 2004/0002734 A1 | 1/2004 | Fallin et al. | | 2006/0253130 A1 | 11/2006 | Wolniewicz |
| 2004/0006345 A1 | 1/2004 | Vlahos et al. | | 2006/0271192 A1 | 11/2006 | Olsen et al. |
| 2004/0006346 A1 | 1/2004 | Holmen et al. | | 2006/0280768 A1 | 12/2006 | Hwang et al. |
| 2004/0015171 A1 | 1/2004 | Bojarski et al. | | 2006/0282085 A1 | 12/2006 | Stone et al. |
| 2004/0015172 A1 | 1/2004 | Biedermann et al. | | 2006/0293709 A1* | 12/2006 | Bojarski et al. ............... 606/232 |
| 2004/0024456 A1 | 2/2004 | Brown et al. | | 2007/0005802 A1 | 1/2007 | Wolniewicz et al. |
| 2004/0087981 A1 | 5/2004 | Berube et al. | | 2007/0016305 A1 | 1/2007 | Chudik |
| 2004/0092936 A1 | 5/2004 | Miller et al. | | 2007/0055255 A1 | 3/2007 | Siegel |
| 2004/0098051 A1 | 5/2004 | Fallin et al. | | 2007/0060922 A1 | 3/2007 | Dreyfuss |
| 2004/0111117 A1 | 6/2004 | Colleran et al. | | 2007/0067025 A1 | 3/2007 | Schwartz |
| 2004/0122431 A1 | 6/2004 | Biedermann et al. | | 2007/0073307 A1 | 3/2007 | Scribner et al. |
| 2004/0133211 A1 | 7/2004 | Raskin et al. | | 2007/0078435 A1 | 4/2007 | Stone et al. |
| 2004/0138664 A1 | 7/2004 | Bowman | | 2007/0083236 A1 | 4/2007 | Sikora et al. |
| 2004/0138683 A1 | 7/2004 | Shelton et al. | | 2007/0093847 A1 | 4/2007 | Scribner et al. |
| 2004/0138704 A1 | 7/2004 | Gambale et al. | | 2007/0142838 A1 | 6/2007 | Jordan |
| 2004/0138706 A1 | 7/2004 | Abrams et al. | | 2007/0185532 A1 | 8/2007 | Stone et al. |
| 2004/0143344 A1 | 7/2004 | Malaviya et al. | | 2007/0239209 A1 | 10/2007 | Fallman |
| 2004/0153103 A1 | 8/2004 | Schwartz et al. | | 2008/0027446 A1 | 1/2008 | Stone et al. |
| 2004/0153153 A1 | 8/2004 | Elson et al. | | 2008/0065114 A1 | 3/2008 | Stone et al. |
| 2004/0162579 A1 | 8/2004 | Foerster | | 2008/0082127 A1 | 4/2008 | Stone et al. |
| 2004/0166169 A1 | 8/2004 | Malaviya et al. | | 2008/0082128 A1 | 4/2008 | Stone |
| 2004/0182968 A1 | 9/2004 | Gentry | | 2008/0132753 A1 | 6/2008 | Goddard |
| 2004/0220574 A1 | 11/2004 | Pelo et al. | | 2008/0132932 A1 | 6/2008 | Hoeppner et al. |
| 2004/0225292 A1 | 11/2004 | Sasso et al. | | 2008/0140092 A1 | 6/2008 | Stone et al. |
| 2004/0236353 A1 | 11/2004 | Bain et al. | | 2008/0140093 A1 | 6/2008 | Stone et al. |
| 2004/0243139 A1 | 12/2004 | Lewis et al. | | 2008/0161852 A1 | 7/2008 | Kaiser et al. |
| 2004/0243178 A1 | 12/2004 | Haut et al. | | 2008/0188936 A1 | 8/2008 | Ball et al. |
| 2004/0249394 A1 | 12/2004 | Morris et al. | | 2008/0255613 A1 | 10/2008 | Kaiser et al. |
| 2004/0267164 A1 | 12/2004 | Rhodes et al. | | 2008/0268064 A1 | 10/2008 | Woodell-May |
| 2004/0267265 A1 | 12/2004 | Kyle | | 2008/0269674 A1 | 10/2008 | Stone |
| 2004/0267270 A1 | 12/2004 | Jacobs et al. | | 2008/0312689 A1 | 12/2008 | Denham et al. |
| 2004/0267276 A1 | 12/2004 | Camino et al. | | 2009/0054928 A1 | 2/2009 | Denham et al. |

| | | |
|---|---|---|
| 2009/0062854 A1 | 3/2009 | Kaiser et al. |
| 2009/0192468 A1 | 7/2009 | Stone |
| 2009/0306711 A1 | 12/2009 | Stone et al. |
| 2009/0312776 A1 | 12/2009 | Kaiser et al. |
| 2009/0318961 A1 | 12/2009 | Stone et al. |
| 2010/0042114 A1 | 2/2010 | Schaffhausen |
| 2010/0145384 A1 | 6/2010 | Stone et al. |

FOREIGN PATENT DOCUMENTS

| | | |
|---|---|---|
| AU | 440266 | 10/1967 |
| AU | 2223767 | 11/1968 |
| AU | 5028569 | 8/1970 |
| AU | 5850469 | 1/1971 |
| AU | 5963869 | 2/1971 |
| AU | 1505470 | 11/1971 |
| AU | 3615171 | 5/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 | 9/1992 |
| GB | 2312376 | 10/1997 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03071962 | 9/2003 |
| WO | WO-03077772 | 9/2003 |
| WO | WO-2005104992 | 11/2005 |

OTHER PUBLICATIONS

"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-JOURNAL 14 pp. 278-284; 1998.
Arthrotek, A Biomet Company; Knees; Sure fire Hybrid Meniscal Device.
Arthrotek, A Biomet Company; Sure fire Hybrid Meniscal Device; Launch Date: Fall AANA 2004.
Bio-Intrafix (TCP/PLA & Intrafix, Tibial Soft Tissue Fasteners, by DePuy Mitek, 6 sheets, (date unknown).
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

"Do your next distal tendon repair with . . . The Lubbers Technique", Teno Fix® brochure, 2003 (2 pages) Ortheon® Medical.

"Make your next tendon repair an open-and-shut case. The Teno Fix® Tendon Repair System", Teno Fix® brochure, 2003 (2 pages) Ortheon® Medical.

US 6,238,418, 05/2001, Schwartz et al. (withdrawn)

\* cited by examiner

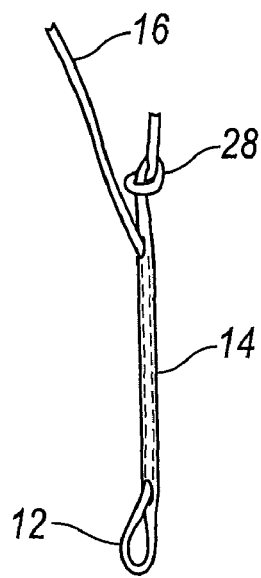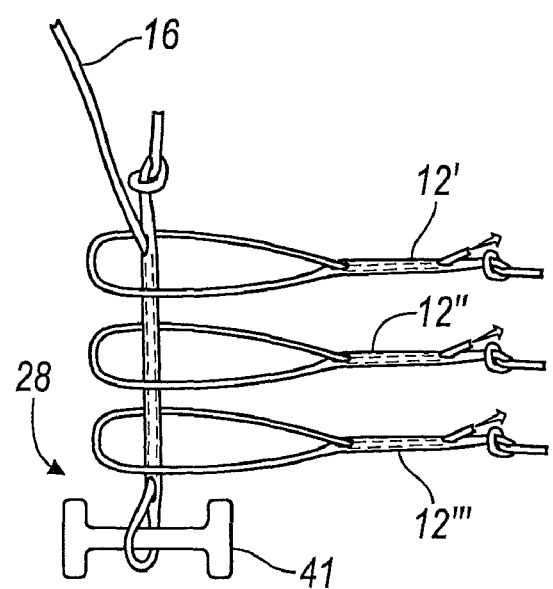
FIG. 12A
FIG. 12B
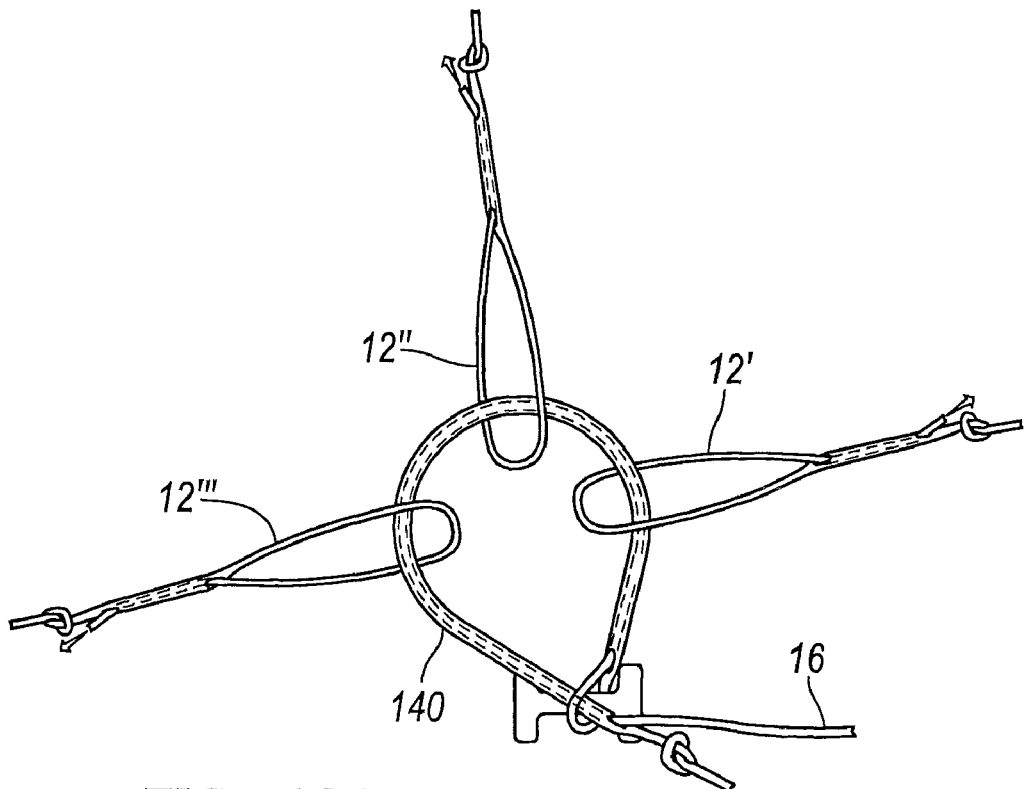
FIG. 12C

ADJUSTABLE KNOTLESS LOOPS

CROSS-RELATED APPLICATIONS

This application is a continuation-in-part of U.S. Ser. No. 11/541,506 entitled "Method and Apparatus for Forming a Self-Locking Adjustable Suture Loop" filed on Sep. 29, 2006; which is now U.S. Pat. No. 7,601,165 U.S. Ser. No. 11/935,681 entitled "Method for Tissue Fixation" and filed on Nov. 6, 2007, to U.S. Ser. No. 11/784,821 entitled "Adjustable Knotless Loops" and filed on Apr. 10, 2007. The aforementioned references are expressly incorporated herein in their entirety.

FIELD

The present disclosure relates to methods and apparatuses for securing a flexible construct. In particular, the present disclosure relates to securing a flexible construct with an adjustable loop.

BACKGROUND

The statements in this section merely provide background information related to the present disclosure and may not constitute prior art.

Surgical procedures are often performed on a body, for example, a human body or anatomy, to repair or replace various portions thereof. For example, the soft tissues of the body may need to be reattached to bones due to trauma, overuse, surgical intervention, or disease.

Soft tissues can be reattached to bone using fastening devices such as screws, staples, and various types of suture anchors. Soft tissues are often fixed to various positions on the bone. For example, to replace a natural tendon fixation point or to replace the tendon itself, fixing a graft to a selected bone area may be desired. One means to fix a soft tissue to the selected area is to provide a suture through a selected portion of the soft tissue and fix the other end of the suture to a selected area on the bone with the fastener. To secure the sutures, the free ends of the suture are tied together to form a knot.

The use of knots in surgical procedures, however, can be improved upon. In minimally invasive procedures, such as arthroscopic or laparoscopic procedures, the surgical site is not readily accessible and limits the surgeon's ability to tie a knot manually. One remote method of securing the suture is tying each of the suture ends into a knot extracorporeally and then remotely advancing the knot into the surgical site using suitably configured instruments. Securing the suture remotely can be cumbersome and time-consuming.

Accordingly, there is a need for improved devices for securing a suture without a knot. There is a need for surgical methods to facilitate easy and efficient securing of the suture.

SUMMARY

The present teachings provide methods of attaching a first tissue to a second tissue. At least one adjustable loop of a flexible construct is passed through at least the first soft tissue. The at least one adjustable loop is passed through a passage construct. A locking member is passed through the at least one adjustable loop and the adjustable loop is reduced about or within the locking member such that the at least one loop is frictionally retained in the passage construct and locked in place by the locking member to thereby secure at least the first tissue.

The present teachings also provide methods of attaching a fist tissue to a second tissue. An adjustable loop is disposed through a bore defined by a fastener. A restriction element of the adjustable loop is secured on a receiving surface of the fastener. The adjustable loop is passed through the soft tissue. The fastener is fixed to an area adjacent the defect such that the adjustable loop and a proximal end of the fastener face the defect. The adjustable loop is then reduced in size to reduce the distance between the anchor and the first tissue.

The present teachings still further provide methods of attaching a first tissue to a second tissue. A first adjustable loop of a first flexible construct contained in a bore defined by a first fastener is passed through at least the first. A second adjustable loop of a second flexible construct contained in a bore defined by a second fastener is passed through the second tissue. The second fastener is attached to the first. The first adjustable loop and the second adjustable loop are passed through a passage construct. A locking member is passed through the two adjustable loops. The first and second adjustable loops are reduced within or about the locking member to thereby attach the first tissue and the second tissue.

The present teachings still further provide methods of attaching a rotator cuff to a bone at a site in need of repair. A first adjustable loop of a first flexible construct contained in a bore defined by a first fastener is passed through the rotator cuff. The first fastener is attached to the bone. A second adjustable loop of a second flexible construct contained in a bore defined by a second fastener is passed through the rotator cuff. The second fastener is attached to the bone at a first position with respect to the first fastener. The adjustable loops are passed over a self-contained locking member and subsequently reduced about the locking member.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 12A through 12C depict a plate type anchor according to various embodiments;

DETAILED DESCRIPTION

Figure 1:
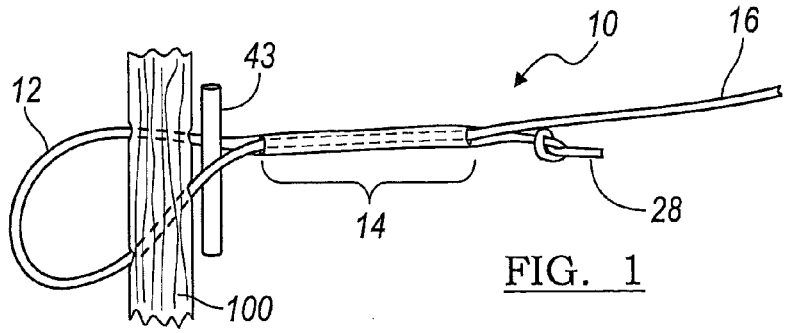
FIG. 1 depicts a flexible construct according to various embodiments.

The following description is merely exemplary in nature and is not intended to limit the present disclosure, application, or uses.

Referring to FIGS. 1-14C, the present teachings provide various surgical methods for connecting a first tissue 100 to a second tissue 200. The first tissue 100 and the second tissue 200 can be independently selected from bone or soft tissue to provide any of a bone-to-bone, a soft tissue-to-bone, or a soft tissue-to-soft tissue connection. The various components used in the surgical methods are presented first and then followed by illustrations of the surgical methods.

Referring to FIGS. 1 through 3B, the flexible construct 10 includes an adjustable loop 12 (or single loop), a passage 14, and an adjusting arm 16. Reduction of the adjustable loop 12 compresses the tissue and provides fixation of the tissue. The adjustable loop 12 and the surgical methods detailed herein, eliminate the need to tie a knot and thereby increase surgical efficiency. As compared to traditional sutures secured by tying a knot, the flexible construct 10 of various embodiments provides increased load to failure, has multiple-fold increased strength, has a decreased stretch at failure, and has multiple-fold stiffness at failure.

Figure 2:
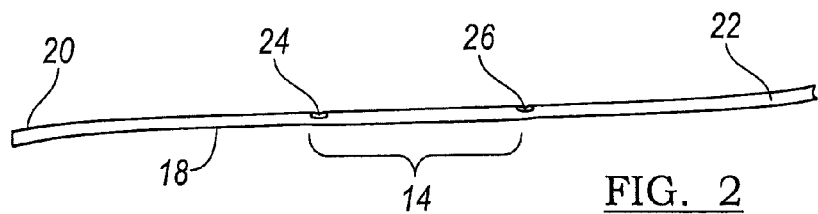
FIG. 2 depicts a fully extended flexible construct according to various embodiments.

Referring to FIG. 2, the flexible construct 10 can be made from any biocompatible material that is flexible and can pass through and secure a tissue. Exemplary materials include, but are not limited to, non-resorbable polymers, such as polyethylene or polyester, resorbable polymers, metals, and various combinations thereof. The materials can include those formed into a monofilament, multiple filaments, cables, and the like. In various embodiments, the flexible construct 10 is made of a hollow material to allow for the appropriate folding and tensioning thereon.

In various embodiments, the flexible construct 10 can be a suture 18. The suture 18 used to form the construct is generally a hollow suture having a distal end 20 and proximal end 22. The suture 18 can be formed as a braided or multiple-filament suture structure that is formed to define a substantially tubular hollow-shaped flexible construct 10.

The suture 18 contains a first opening 24 located closer to the distal end 20 and the second opening 26 located closer to the proximal end 22. In various embodiments, the first opening 24 and the second opening 26 can extend along a top surface of the suture 18 and are sized to accommodate passage of the distal end 20 of the suture therethrough. It is understood that the first opening 24 and the second opening 26 need not be formed by cutting the suture 18 or by removing any suture material. For example, the first opening 24 or the second opening 26 can be formed by passing the suture distal end 20 through the sidewall of the hollow tubular suture 18.

The passage 14 is defined by the area between the first opening 24 and the second opening 26. The passage 14 can be a short passage, can extend to the length of a fastener used therewith, or have a greater length, as further detailed later herein.

To provide the adjustable loop 12 and the adjusting arm 16, the distal end 20 of the suture 18 is passed through the first opening 24, into and through the passage 14, and advanced out of the second opening 26. The portion exiting from the second opening 26 provides the adjusting arm 16 and the folded end provides the adjustable loop 12.

Figure 3A:
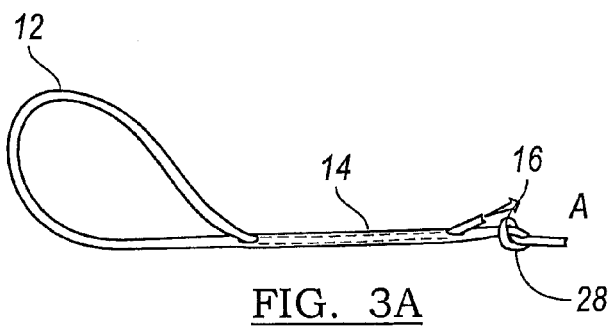
FIGS. 3A and 3B depict movement of the adjustable loop according to various embodiments.
Figure 3B:
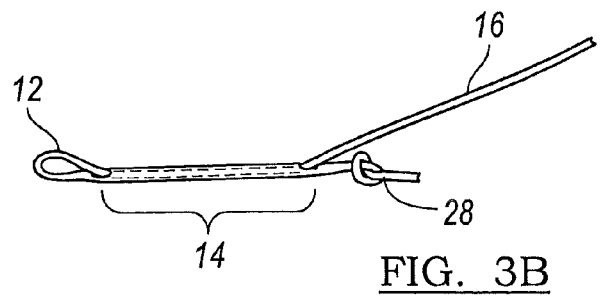

Referring to FIGS. 3A and 3B, the adjusting arm 16 is engaged or pulled in direction A to cause movement of the adjustable loop 12. As the adjustable loop 12 is reduced in size (or creating a smaller diameter loop 12), the adjusting arm 16 lengthens, as shown in FIG. 3B. In various embodiments, the movement of the suture 18 is only in the direction of arrow A and movement is prevented in the opposite direction. This unidirectional movement is controlled by maintaining tension (by pulling, for example) on the flexible construct 10 to radially compress the passage 14 about the suture portion contained therein as further detailed later herein.

To facilitate the unidirectional movement, a restriction element 28 can be included near the proximal end 22. The restriction element 28 controls movement of the adjustable loop 12 and the adjusting arm 16. Moreover, the restriction element 28 can prevent displacement of the flexible construct 10 in minimally invasive procedures. As depicted, the restriction element 28 is a knot. It is understood that the restriction element 28 does not provide the tissue fixation, but it is the tissue compression provided by the reduction of the adjustable loop 12 about the tissue that provides the fixation. The restriction element 28 can include other devices used to retain a suture, such as a suture clip.

Figure 4:
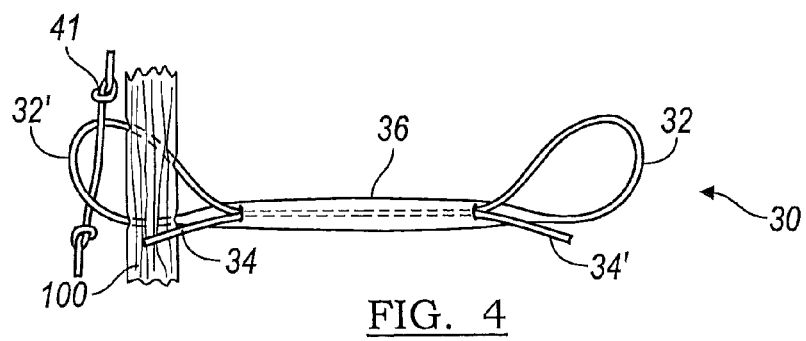
FIG. 4 depicts a flexible construct comprising two adjustable loops according to various embodiments.

Referring to FIG. 4, in further embodiments, a flexible construct 30 provides two adjustable loops 32 and 32' (or a double loop) on a single construct. Similar to the single adjustable loop of flexible construct 10 as detailed above, the adjustable loops 32 and 32' are reduced by engaging the respective adjusting arms 34 and 34'. For example, upon engaging the adjusting arm 34, the length of the flexible member forming the adjustable loop 32 is reduced as the material is passed through the passage 36. The movement of the adjusting arms 34 and 34' and thus the reduction of the adjustable loops 32 and 32' occur independently. Movement of the adjusting arms 34, 34' and the subsequent reduction of the adjustable loop 32, 32' size are generally unidirectional due to friction of the construct components within the passage 36. A further discussion of the various loops that are useful with the present teachings are disclosed in U.S. patent application Ser. No. 11/541,506 to Stone, filed Sep. 29, 2006 and U.S. patent application Ser. No. 11/784,821 to Kaiser et al. filed Apr. 10, 2007, and assigned to Biomet Sports Medicine, Inc., which are both incorporated by reference.

Figure 5A:
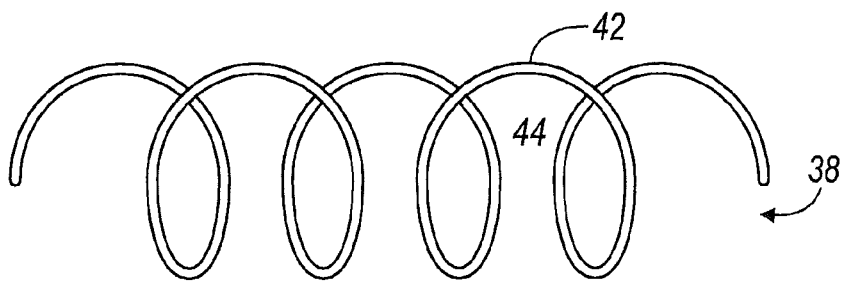
FIGS. 5A-5B depict various pathway constructs according to various embodiments.
Figure 5B:
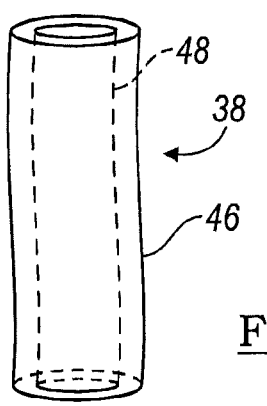

Referring to FIGS. 5A and 5B, a pathway construct 38 provides a passage that is used to guide, contain, or otherwise engage the flexible constructs 10 or 30. In various embodiments, the flexible constructs 10, 30 can be disposed about an exterior of the pathway construct 38. As will be detailed further in the discussion of FIGS. 7A-7D and 8A-9C, the pathway construct 38 can be created from another component in the system. The pathway constructs 38 are used to guide the flexible member construct 10 or 30 and can serve to keep the adjustable loop 12 in proper orientation during the surgical procedures.

Figure 6A:
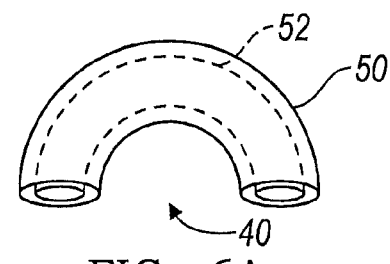
FIGS. 6A-6D depict various locking members according to various embodiments.
Figure 6B:
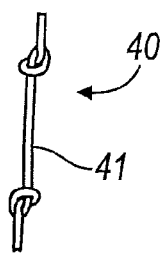
Figure 6C:
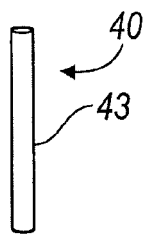
Figure 6D:
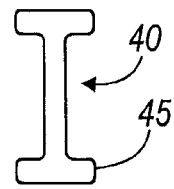

Turning to FIGS. 6A-6D, and as is illustrated in FIGS. 1 and 4, a locking member 40 is provided in the loops 12 or 32, 32' of the flexible members 10 or 30 respectively. In various embodiments, the locking member 40 can be an integral part of the adjustable loop 12 or another portion of the flexible construct, or the locking member 40 can be a separate piece, such as the use of the restriction element 28 as a locking member depicted in FIG. 7D. As shown in FIG. 6A, the locking member 40 can be an elbow 50 which defines a through passage 52 to receive a region of a suture 51, for example. In other embodiments, the locking member 40 can be a construct 41 made of a length of a flexible material having two knots located at the ends thereof as shown in FIGS. 4 and 6B, a tubular member 43 as shown in FIGS. 1 and 6C, or an I-shaped or dumbbell shaped member 45 as shown in FIG. 6D.

The locking member 40 secures and/or prevents the adjustable loops 12 or 32, 32' of the flexible members 10 or 30, respectively from being pulled back out of the tissue. The locking member 40 allows the adjustable loop portion 12 or 32 of the flexible construct 10 or 30, respectively, to rotate or slide so that the adjustable loop 12 does not "catch" on the locking member 40 prior to achieving the desired end size reduction or compression. The locking member 40 functions to prevent the adjustable loops 12 or 32, 32' from pulling out of the tissue, to prevent the adjustable loops 12 or 32, 32' from pulling out of the pathway construct, to tighten and/or securing of the tissue, and combinations thereof.

The flexible constructs 10 and 30 are useful in the various methods disclosed herein. The flexible constructs 10 and 30 and surgical techniques detailed herein can be used with various repairs of the shoulder, wrist, hand, ankle, foot, elbow, knee, or hip as non-limiting examples. The embodiments detailed herein are particularly useful in repairing certain soft tissue defects, for example, a labral tear. Exemplary repairs include Bankart Repair, SLAP Repair, Acromioclavicular separation, rotator cuff repair, capsule repair or capsulolabral reconstruction, biceps tenodesis, or deltoid repair of the shoulder; scapholunate ligament reconstruction or ulnar radial collateral ligament reconstruction of the wrist or hand; lateral stabilization, medial stabilization, Achilles tendon repair and reconstruction, halux valgus reconstruction, midfoot reconstruction, and forefoot reconstruction of the ankle or foot; lateral epicondylitis (tennis elbow) repair, ulnar or radial collateral ligament reconstruction, and biceps tendon reconstruction of the elbow; and extra-capsular repair, medial collateral ligament repair, lateral collateral ligament repair, posterior oblique ligament repair, joint capsule closure, iliotibial band tenodesis reconstruction, patellar realignment and repair, patellar ligament and tendon repair, and vastus medialis obliquus muscle advancement. It is understood that the techniques detailed herein can be used for orthopedic repair including cartilage repair, ligament repair, or tendon repair. The repair can be with an articular orthopedic surface or a non-articular and/or non-orthopedic surface.

Although an illustration of a particular embodiment may include a depiction of only the single loop flexible construct 10 or the double loop flexible construct 30, the embodiments and teachings herein are not so limited. It is understood that the preparation of the various constructs and assemblies detailed herein can be performed extra corporeally or at/within the surgical site. The various surgical methods allow tissue fixation without requiring the surgeon to tie knots in the flexible members.

Figure 7A:
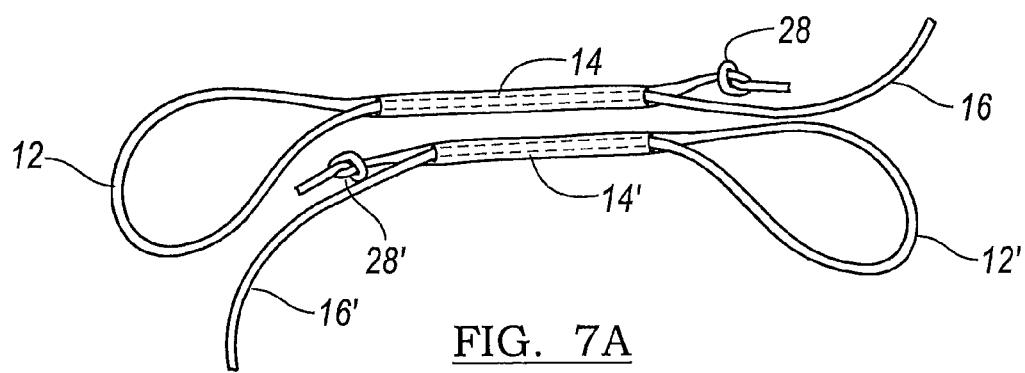
FIGS. 7A-7D depict a system employing a coiled flexible member pathway construct according to various embodiments.
Figure 7B:
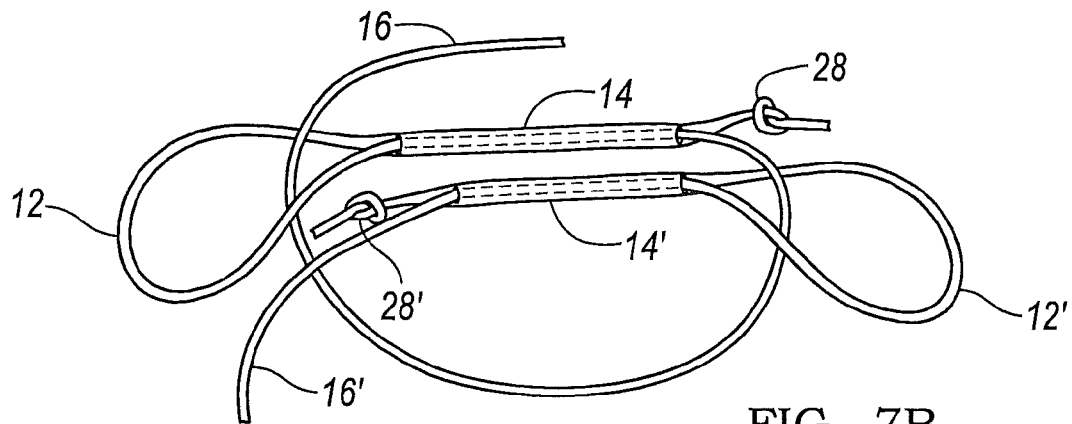
Figure 7C:
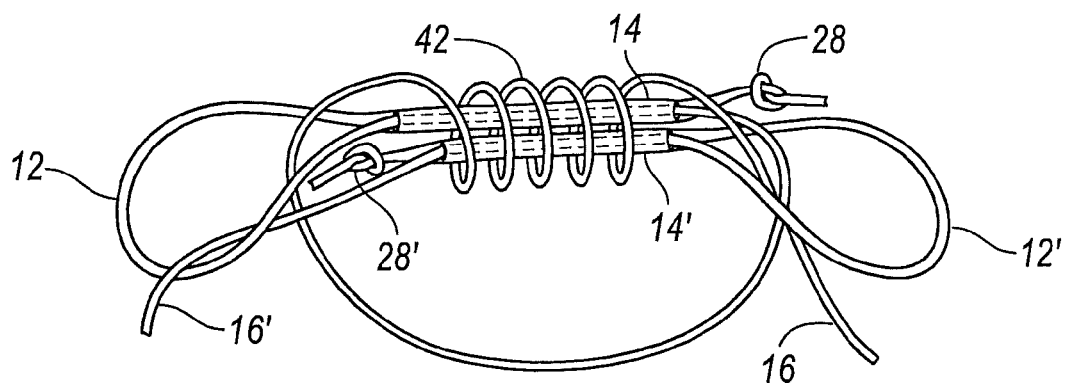

FIGS. 7A-7D depict a first surgical method according to the present teachings. Two flexible member constructs 10 and 10' are aligned such that the passages 14 are immediately adjacent as shown in FIG. 7A. Next, the adjustable loop 12 or a region of the passage 36 is passed through the interior or about an exterior of a pathway construct 38 shown as coil 42. The coil 42 is formed by wrapping a length of the adjusting arm 16 about a region of the adjustable loop 12, such as the passage 14. This wrapped system is similar to the coil preparation and flexible member securing referred to as a "Duncan loop" 42 to fishing hobbyist. Engaging or pulling the adjusting arm 16 which forms part of the Duncan loop causes the coil 42 to reduce about each respective passage 14 and 14' of the adjustable loops 12 and 12'.

Figure 7D:
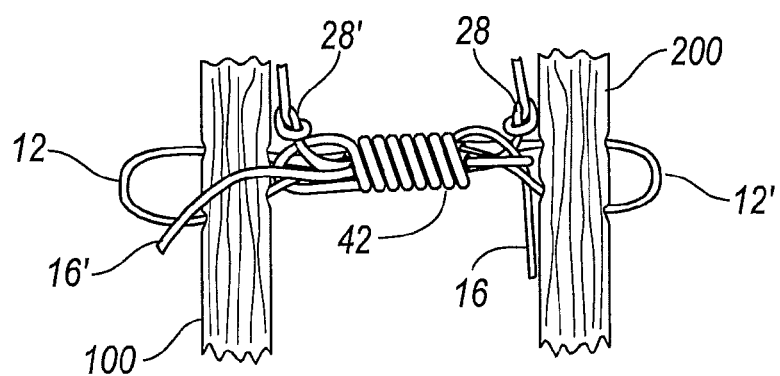

The securing elements 28 and 28' of each adjustable loop 12 and 12', respectively, are then passed through the opposing adjustable loop. As shown in FIG. 7D, the securing element 28 is passed through the adjustable loop of 12' and the securing element 28' is passed through the adjustable loop 12. The securing elements 28 and 28' serve as the locking member 40 for the opposing adjustable loop.

Next, the adjustable loop 12 is passed through the first tissue 100 and a second adjustable loop 12' is passed through the second tissue 200. Where a soft tissue is used, the adjustable loop 12 can be passed through the soft tissue by piercing a hole in the tissue prior to passing the adjustable loop 12 therethrough. This can be performed with a separate needle, a needle that is removably attached to the adjustable loop 12 or, in embodiments using a separate fastener, such as those illustrated later herein, with a tip of the fastener. Any suitable suture passer or other device can also be used to pass the adjustable loop 12 through the tissue such as those known in the art as "bird beak" passers or suture lariats. Two devices useful for passing the suture include those sold under the tradenames SpeedPass and ArthroPass, both made by Biomet Sports Medicine, Inc. of Warsaw, Ind. In embodiments where a hard tissue such as bone is one of the tissues 100 or 200, a bore can be placed in the bone to receive the adjustable loop 12 or a region of the flexible member construct 10. As shown in FIGS. 7A and 7D, the adjustable loop region 12 passes through the tissue 100 or 200 and a loop end 13 extends out of the tissue 100 or 200.

After the adjustable loops 12 and 12' are passed through the tissue and the restriction elements 28 and 28' are arranged to facilitate the tissue and adjustable loop securing, adjusting arms 16 and 16' are engaged. This causes the coil 42 and the adjustable loops to be reduced in size, as shown in the transition from FIG. 7C to FIG. 7D. The securing elements 28 and 28' serving as the locking members 40 prevent the adjustable loops 12 and 12' from passing back out of the tissue, and serve to increase the securing of the adjustable loops 12 and 12' at the tissue. The first tissue 100 and the second tissue 200 are brought in close proximity to effectuate securing. It is understood that the first tissue 100 and the second tissue 200 need not be discrete portions of tissue, but can be regions of the same area, for example, a partially torn rotator cuff.

Referring to the second embodiment of this group, as shown in FIGS. 5B, 8A-8D, 9A-9C, a tubular flexible member 46 defines the pathway construct 38 and the locking member 40. The tubular flexible member 46 can be a suture or any suitable flexible material, such as those listed above herein, which is sufficiently wide to accommodate the adjustable loops 12 or the adjustable loops 32 and 32'. In various embodiments, the tubular flexible member 46 can be a #2-0 to a #2 suture.

Specifically turning to FIGS. 8A-8D, the tubular flexible member 46 includes end openings 54 and 54' at each end thereof. To prepare the tubular flexible member 46, the tubular flexible member 46 is folded in half, and flexible construct receiving openings 56 and 56' are prepared therein. The flexible construct receiving openings 56 and 56' can be prepared by spreading a region of a braided suture material or by cutting a region of the tubular flexible member 46, for example, with a suture threader 58. The flexible construct receiving openings 56 and 56' are generally aligned with the end openings 54 and 54', respectively to define the pathway construct 38.

After defining the pathway construct between the openings 54 and 56 and 54' and 56', respectively, adjustable loops 12 and 12' are passed through eyes 60 and 60' of the suture threader 58. The adjustable loops 12 and 12' can be passed by hand or using a guide wire. The suture threader 58 loaded with the adjustable loops 12 and 12' is then advanced axially downwardly through the arms of the tubular flexible member 46 such that the adjustable loops 12 and 12' extend out of the openings 56 and 56'.

Figure 8A:
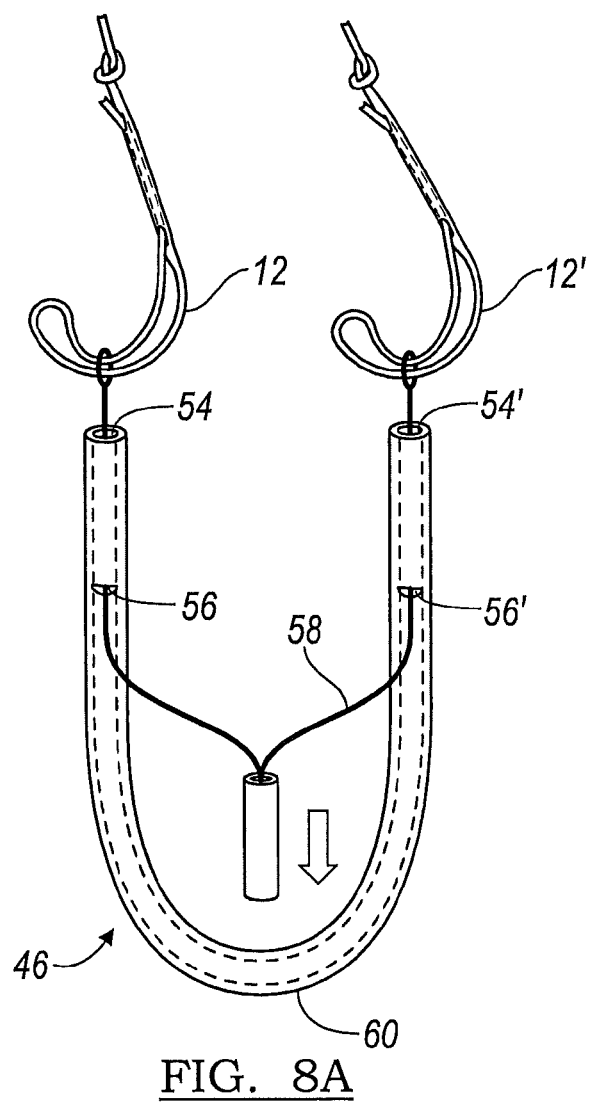
FIGS. 8A-8D depict a tubular flexible member pathway construct according to various embodiments.
Figure 8B:
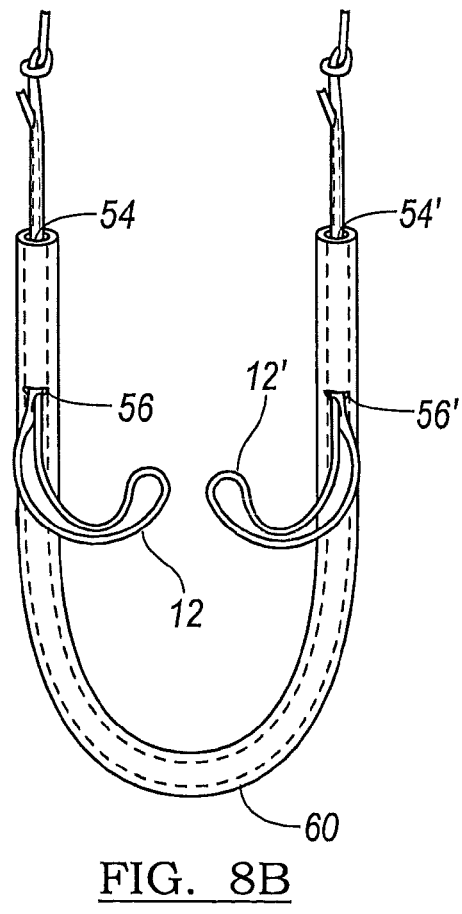
Figure 8C:
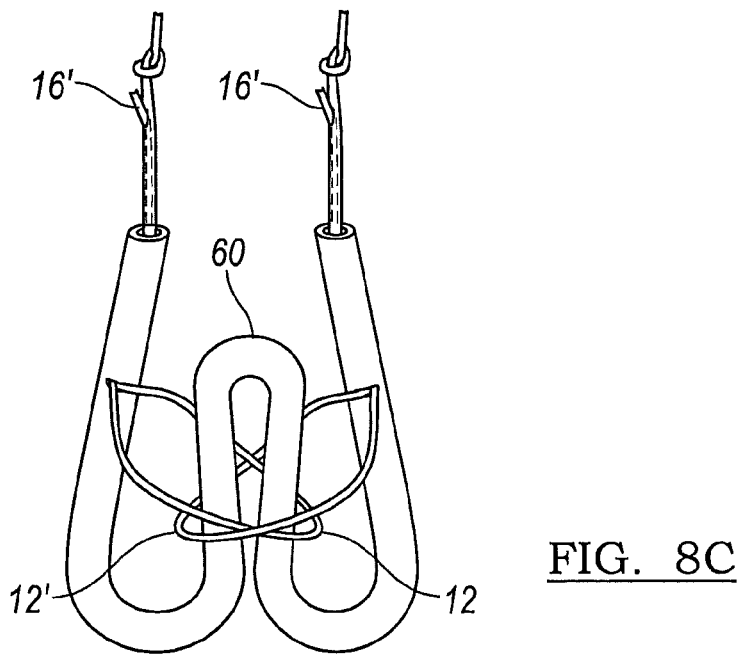
Figure 8D:
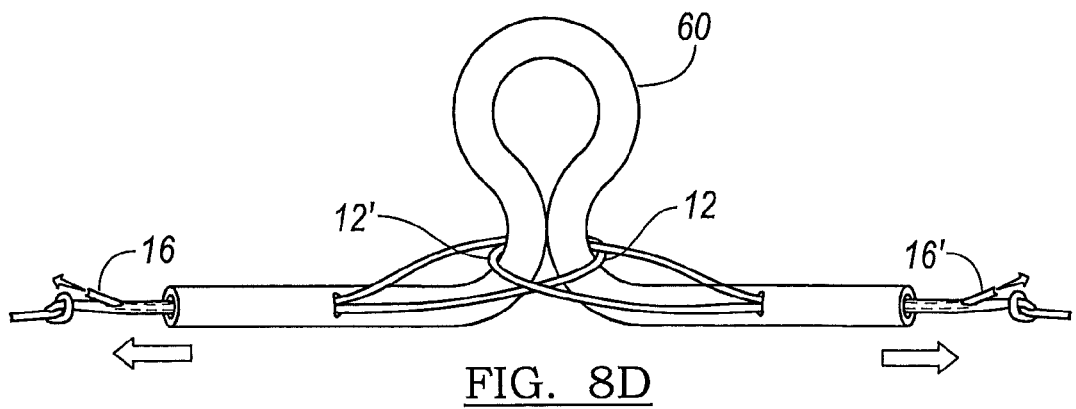

Continuing the assembly illustration at FIG. 8B, a bend 60 of the tubular flexible member is passed through the two adjustable loops 12 and 12'. When completely advanced, the bend 60 is trapped between the interlaced adjustable loops 12 and 12'. In this embodiment, the bend 60 serves as the locking member 40 and upon advancing the adjusting arms 16 and 16', the adjustable loops 12 and 12' compress about the bend 60 and thereby frictionally lock the assembly. It is understood that the additional locking member 40 such as the cylinder or bar 43 of FIG. 6C can also be used in the assembly to prevent slippage. In this embodiment, the adjustable loops 12 and 12' can be placed in the tissue 100 and also, the tubular flexible member 46 can be placed in the tissue 100.

Figure 9A:
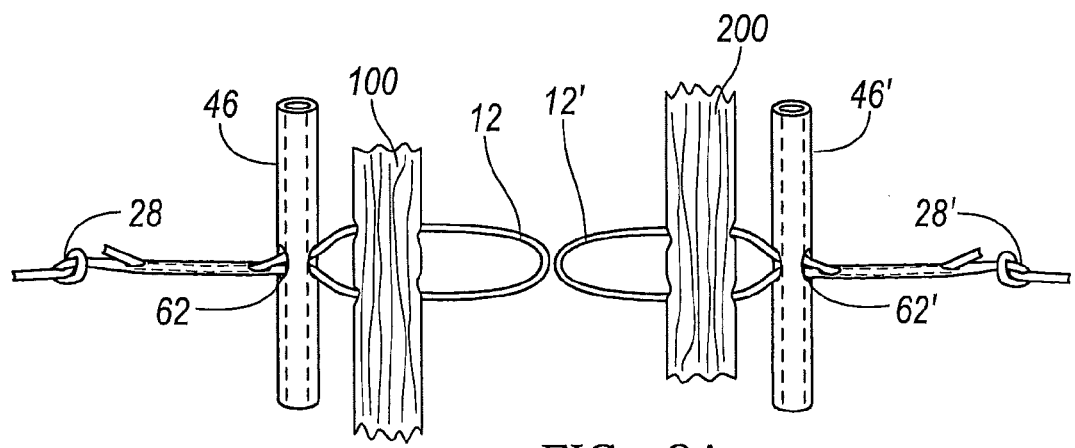
FIG. 9A-9C depict multiple tubular flexible member pathway constructs according to various embodiments.
Figure 9B:
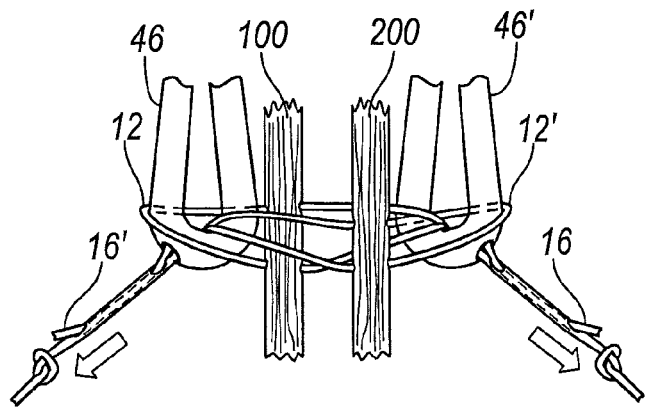
Figure 9C:
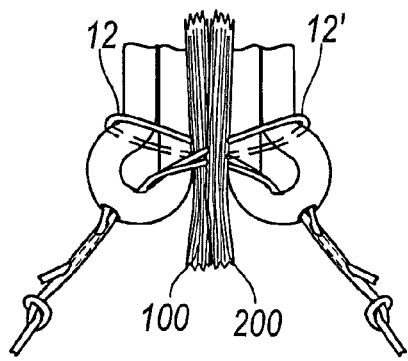

Turning to FIGS. 9A-9C, in a third embodiment of this grouping, a plurality of tubular flexible members 46 and 46' can be used to provide the assembly. Transverse openings 62 and 62' are placed in the respective tubular flexible members 46 and 46'. The adjustable loops 12 and 12' are passed through the respective transverse openings 62 and 62' as shown in FIG. 8A. The adjustable loops 12 and 12' can be passed through the first and second tissue 100 and 200 as detailed above.

The tubular flexible members 46 and 46' are then folded and disposed in the adjustable loop 12' and 12 of the opposing flexible member 46 and 46'. This causes the adjustable loops 12 and 12' to become interlaced. Upon engaging the adjusting arms 16 and 16' in the direction of the arrow, the adjustable loops 12 and 12' compress about the tubular flexible members 46 and 46' to frictionally secure the construct. Similar to the embodiment of FIGS. 7A-7D, regions of the tubular flexible members 46 and 46' serve as both the pathway construct and as the locking member. The tubular flexible members 46 and 46' and/or the adjustable loops 12 and 12' can be used to secure the tissue.

Figure 10A:
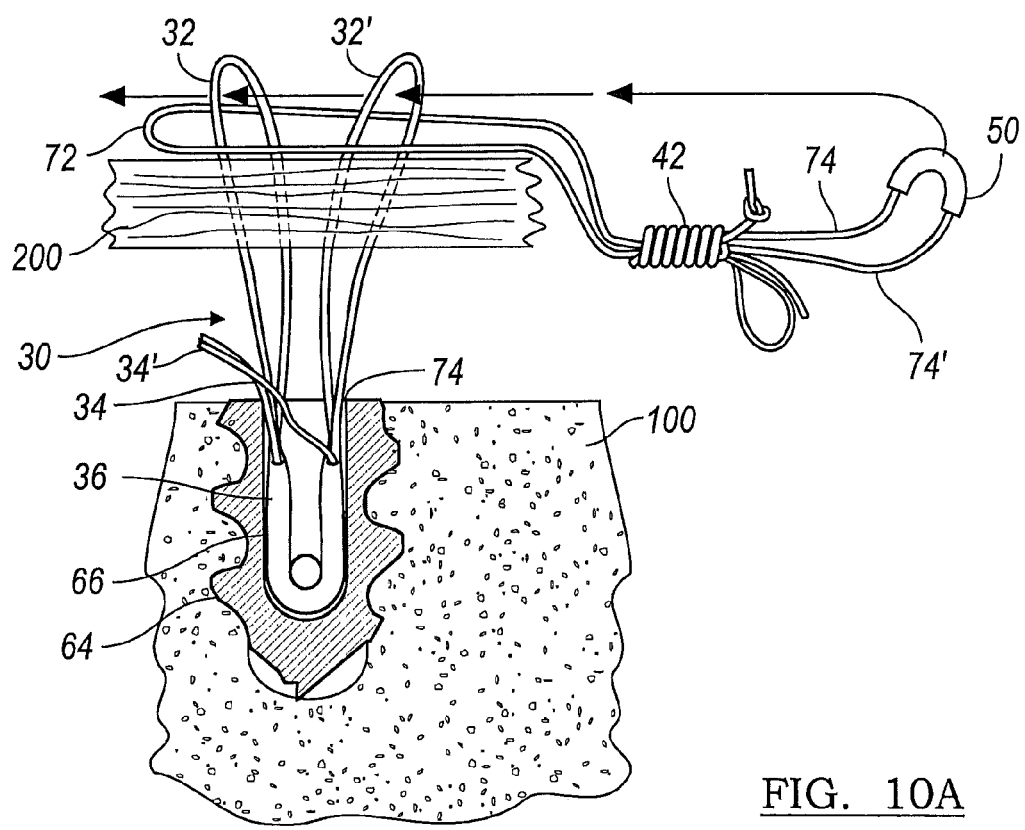
FIGS. 10A-10C depict an elbow shaped flexible member pathway according to various embodiments.
Figure 10B:
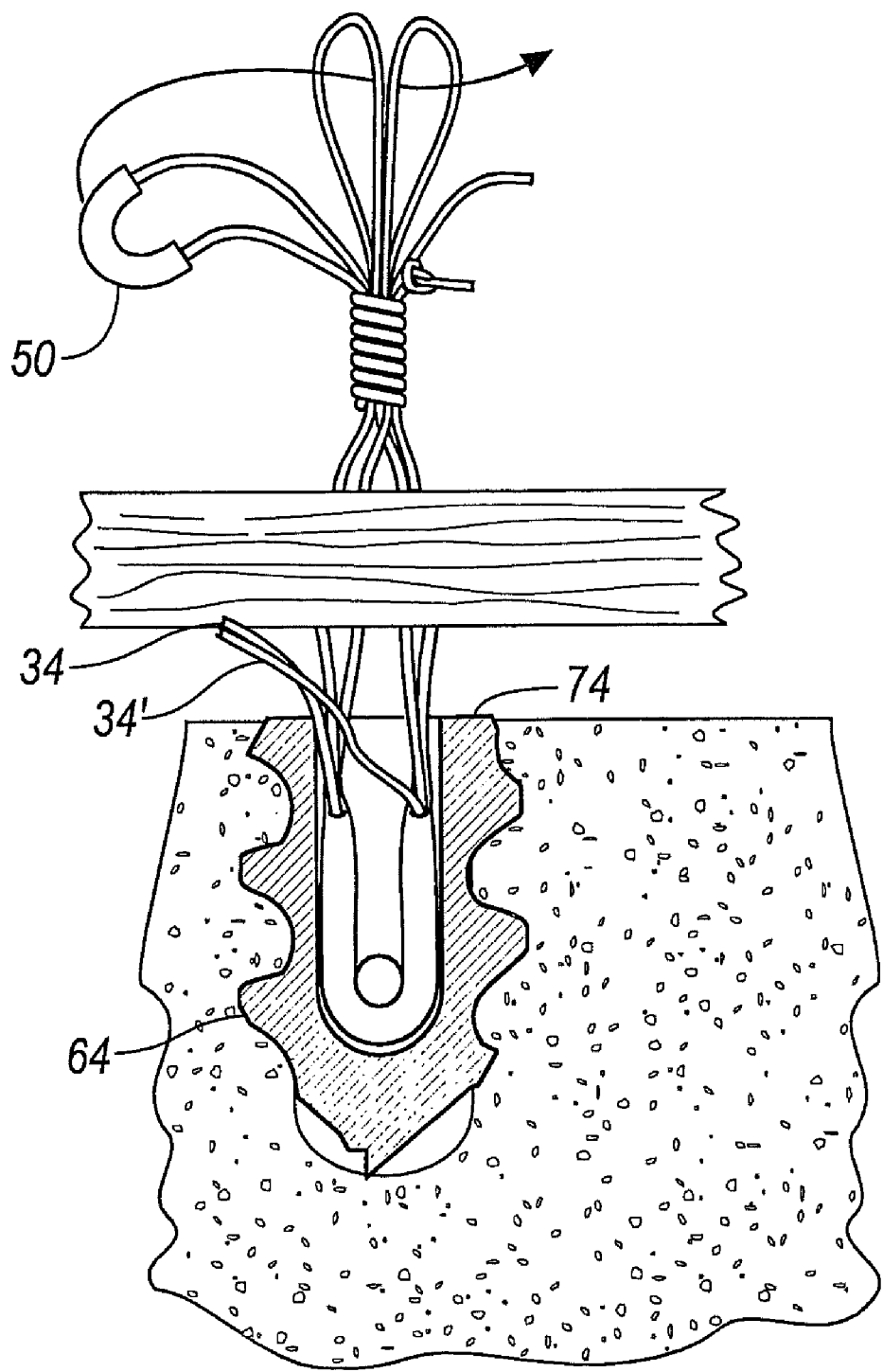
Figure 10C:
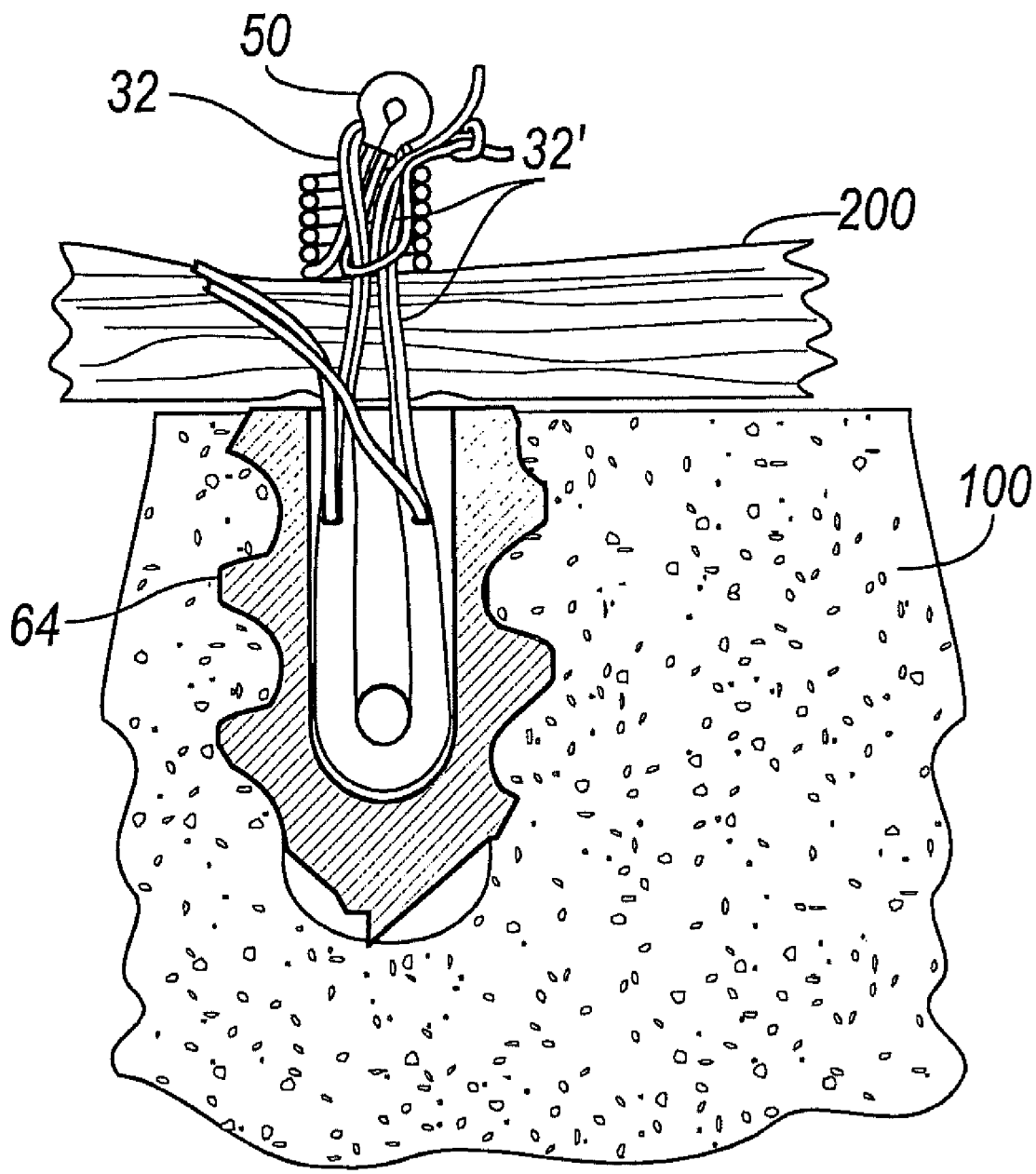

In a fourth embodiment of this grouping as shown in FIGS. 6A and 10A-10C, which is depicted with the flexible member 30, an elbow 50 locking member is employed and a suture anchor 64 serves as the pathway construct. As best shown in FIGS. 10A and 10C, this embodiment can be used to fix bone as the first tissue 100 via the suture anchor 64 and cartilage or a tendon as the second tissue 200 via the adjustable loops 32 and 32'. It is understood that the teachings are not limited to suture anchors but also include a button, a clip, or another suture-retaining device. The various suture anchors detailed herein can be made of any biocompatible material including, but not limited to, a metal, such as titanium, stainless steel, or alloys of cobalt, chromium, etc., or a polymer such as polyetheretherketone (PEEK) or polymers and copolymers of lactic and glycolic acid.

In use, the passage 36 of the flexible construct 30 is passed into a bore 66 defined by the interior of the anchor 64. The flexible construct can be passed through the interior of the anchor 64 using a guide wire or by hand. The anchor 64 is then placed into the bone first tissue 100, such as through a predrilled hole in the boney first tissue 100. It is also understood that a self-tapping anchor or other fastener can be used to provide the pathway construct in the boney first tissue 100.

Next, the adjustable loops 32 and 32' are passed through the tissue as detailed above. Subsequently, the elbow 50 locking member is disposed at the end of a Duncan loop 68 to create an assembly 70. The assembly is then formed by taking a length of a flexible material and passing it through the elbow 50 such that at least a portion of the flexible material extends from both sides of the elbow 50 to form arms 74 and 74'. The arm 74 is folded and repeatedly wrapped around arm 74' to provide a coil of flexible material, as was illustrated in FIGS. 7B-7D. The Duncan loop 68 can be secured with a knot or using one of the locking members of FIGS. 6A-6C.

Next, a summit 72 region of the assembly 66 is passed over the two loops 32 and 32' which extend from anchor 64. The flexible material is advanced to reduce the length of the summit 72 region, and the elbow 50 is passed through the loops 32 and 32' following the path as indicated by the arrows in FIG. 10A. Upon engaging the adjusting arms 34 and 34', the elbow 50 is drawn down towards a proximal end 74 of the anchor 64 such that the elbow 50 locking member faces or abuts the proximal end 74. The placement of the elbow 50 at the proximal end 74 fixes the flexible member 30 in the pathway construct of the anchor 64. In various embodiments, the elbow 50 can be used in conjunction with or replaced with a large knot in the assembly. Additional examples employing a suture anchor pathway construct are detailed later herein.

Referring to FIGS. 11A-11H, in the next group of embodiments, the present teachings also provide methods of attaching a first boney tissue 100 using a fastener 92 to a second soft tissue 200 using the flexible construct 10. The fastener 92 includes a fastener body 94 which extends between a proximal end 96 and a distal end 98, an axially extending interior bore 102, and at least one side bore 104 which is generally perpendicular to the interior bore 102. In various embodiments, the fastener 92 includes a plurality of side bores 104. In various embodiments, the axially extending bore 102 can have a proximal end opening which is mated to receive a tool, such as a driver for inserting the anchor, as are well known in the art.

Figure 11A:
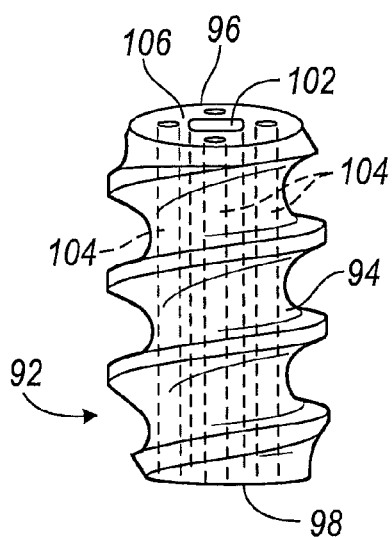
FIGS. 11A-11H depict a surgical technique using multiple flexible constructs according to various embodiments.
Figure 11B:
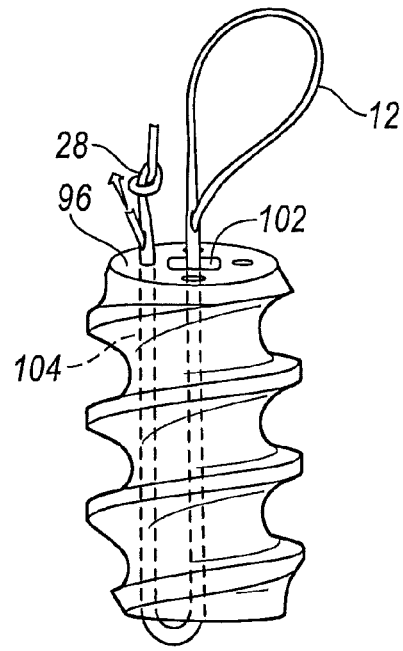
Figure 11C:
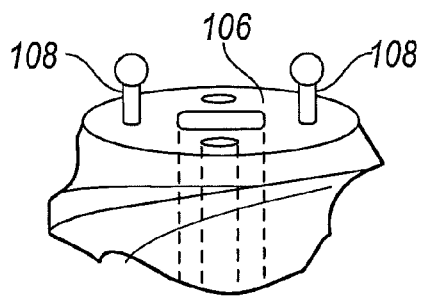
Figure 11D:
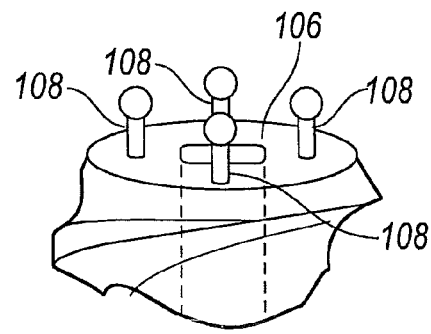
Figure 11E:
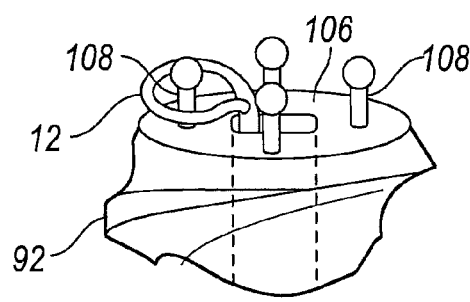

At the proximal end 96 of the fastener 92, is a receiving surface 106 used to receive a region of the flexible construct 10. As depicted in FIG. 12A, the receiving surface can be a flat surface which is flush with the receiving surface 106. As shown in FIGS. 11C-11E, the receiving surface 106 can also include various combinations of posts 108 designed to hold the adjustable loop 12 region of the flexible construct 10.

In use, the flexible construct 10 is disposed downwardly into the side bore 104 such that the restriction element 28 faces or abuts a flat or recessed region of the receiving surface 106 which is defined by the region adjacent to the opening for the side bore 104. The restriction element 28 is sized such that it is too large to pass through the side bore 104. The adjustable loop region 12 is then passed upwardly towards the proximal end 96 of the fastener through the interior bore 102 such that the adjustable loop 12 extends from the proximal end 96 of the fastener and is free for suturing of the soft tissue 100. After securing the adjustable loop 12 to the soft tissue 100, the adjusting arm 16 of the flexible construct 10 is engaged to cause reduction of the adjustable loop 12. The posts 108 at the proximal end 96 of the fastener can be used to retain the adjustable loop 12, as shown in FIG. 11E.

Figure 11F:
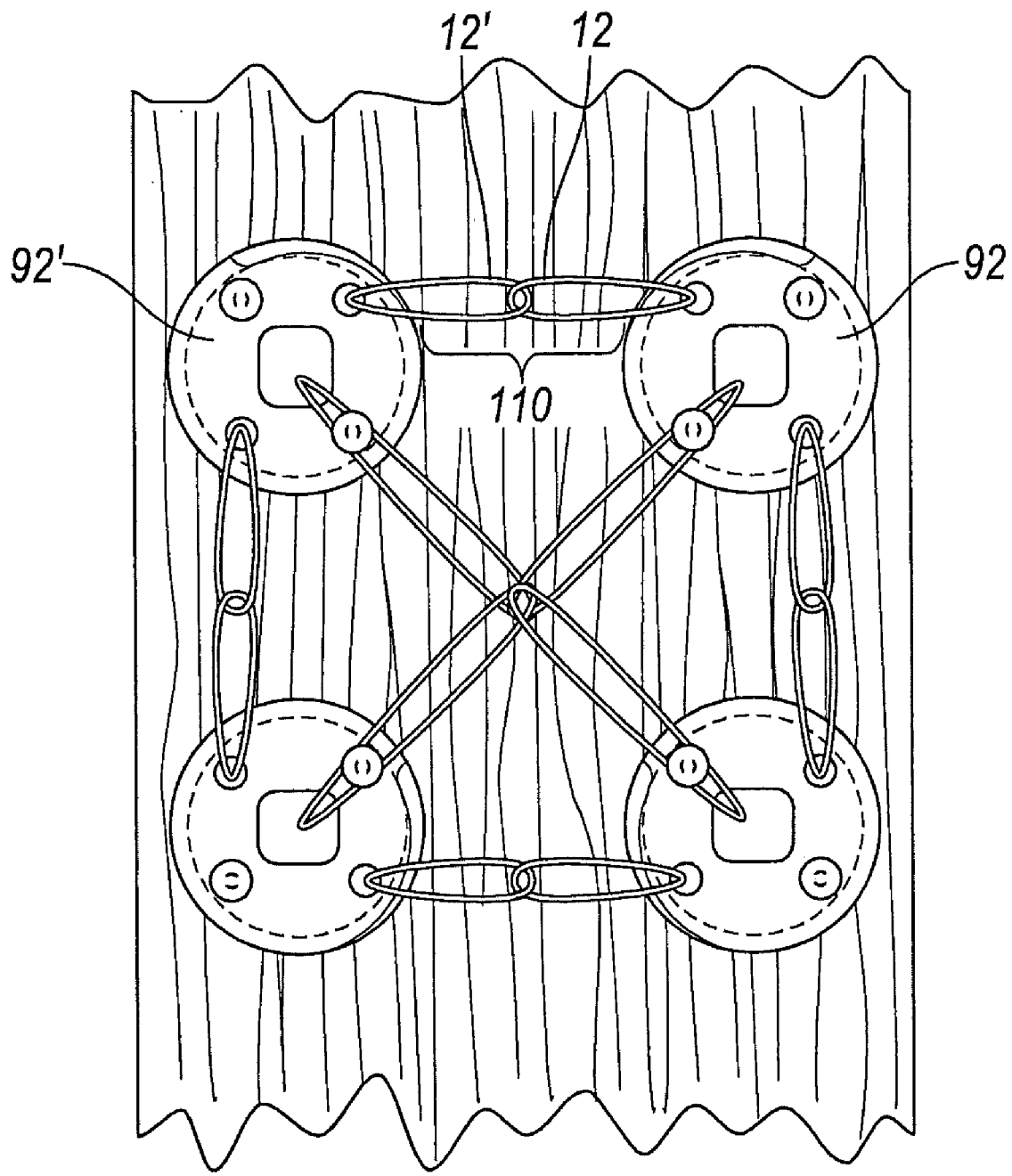
Figure 11G:
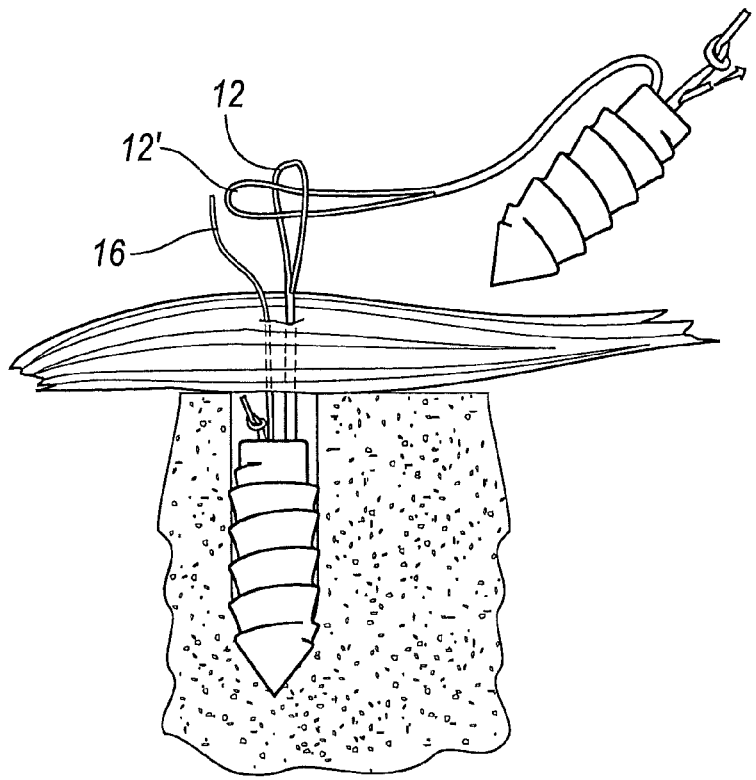
Figure 11H:
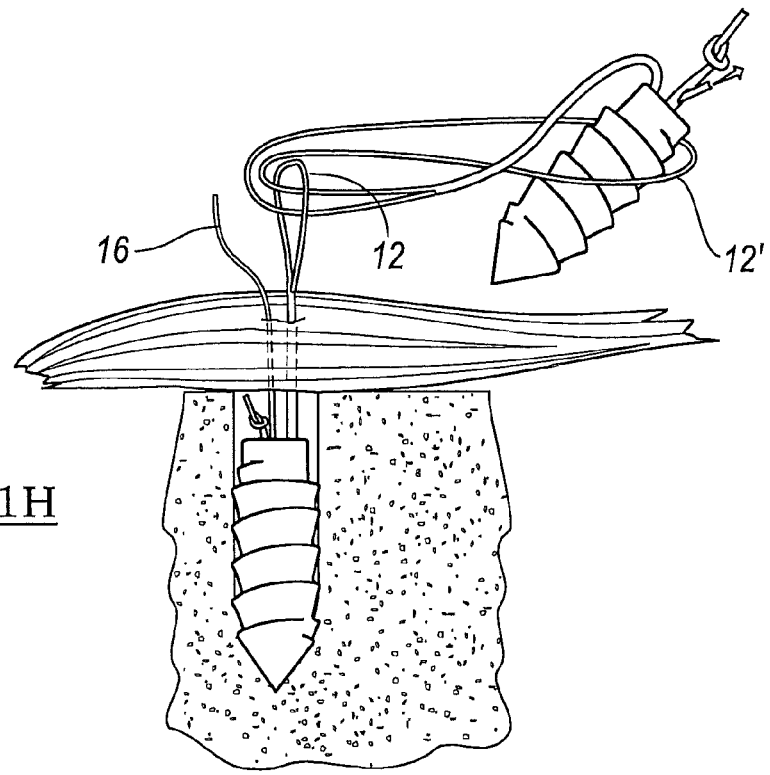

Turning to multiple fastener embodiment of FIG. 11F, a plurality of fasteners 92 and flexible constructs 10 are connected to form an interlaced web or bridge 110 of adjustable loops 12. As shown in FIGS. 11G and 11H, the fastener 92 is first placed in the boney first tissue 100 and has the adjustable loop 12 extending from the distal end of the fastener 92. A second fastener 92' having an adjustable loop 12' thereon is then passed through the adjustable loop 12. The adjustable loop 12' is then wrapped back around the fastener 92' to interlace the adjustable loops 12 and 12'. This process is repeated until the desired number of fasteners is placed at the site in need of tissue repair.

The pattern of the flexible constructs and the placement of the adjustable loops 12 can be varied as needed by the user after evaluating the soft tissue defect to provide a specialized retention and securing of the soft tissue 100. The adjustable loops 12 can be reduced in size using the respective adjusting arms 16 to retain the fastener 92 proximal end 94 in abutment with the soft tissue 200 or to reduce the distance between the anchor and the first tissue.

To start, a first fastener 92 is inserted into a pre-drilled hole in the bone and the first adjustable loop 12 is on top of the tissue. A second fastener 92' is then passed through the first adjustable loop 12 and folded back into the second adjustable loop 12' to interlace the adjustable loops 12 and 12'. The second fastener 92' is then secured through the tissue 100 and into the bone. The first adjusting arm 16 is then engaged to cause the respective loops to reduce in size and form a link or bridge 110 of interlaced adjustable loops 12 and 12' between the first fastener 92 and the second fastener 92'. The interlacing and sequential tightening is continued until the desired numbers of fasteners are placed at the defect. After the adjusting arms 16, 16' are engaged to the correct distance to reduce the respective adjustable loops and provide the appropriate amount of tissue compression and securing at the defect site, the adjusting arms 16 and 16' can be optionally cut. There is no need for the surgeon to tie a knot as the interlaced and compressed loops provide the tissue fixation. As illustrated, each fastener 92 can provide a plurality of connections.

Turning to FIGS. 14A-14D, the fastener 92 can further include a plate portion 112. The plate portion 112 includes a tip 114 and a panel 116 extending from the tip 114. The panel 116 further includes a post 118 and defines at least one suture receiving openings 120. In various embodiments, the panel includes a plurality of suture receiving openings to accommodate multiple flexible constructs 10. The suture receiving openings 120 can independently be offset from the longitudinal axis of the plate portion 112 or can be centered therewith.

Figure 14A:
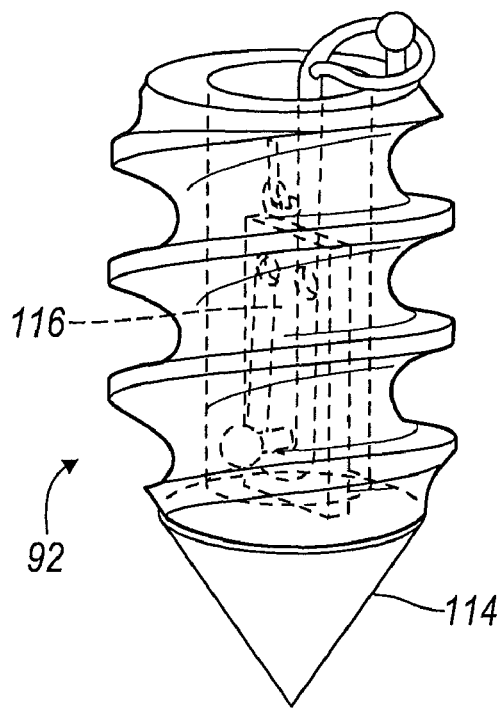
FIGS. 14A-14D depict a surgical method employing the folded tubular flexible member pathway construct according to various embodiments.
Figure 14B:
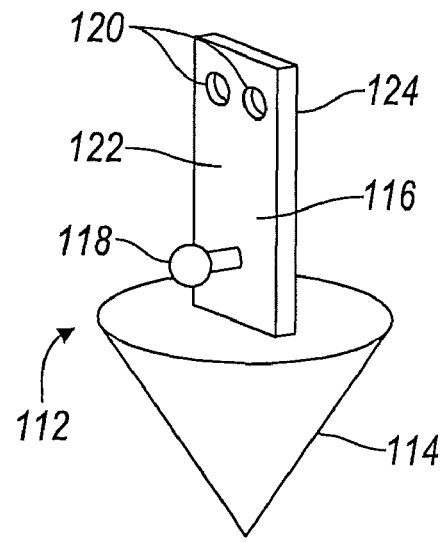
Figure 14C:
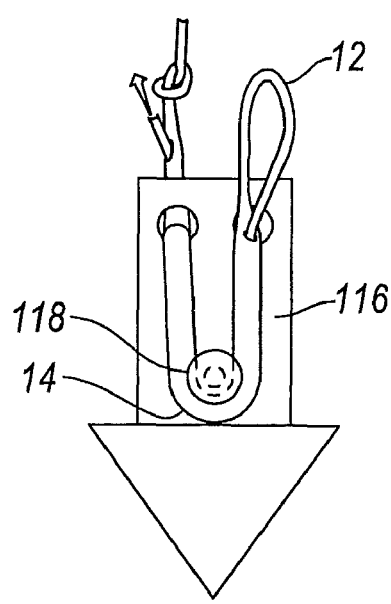
Figure 14D:
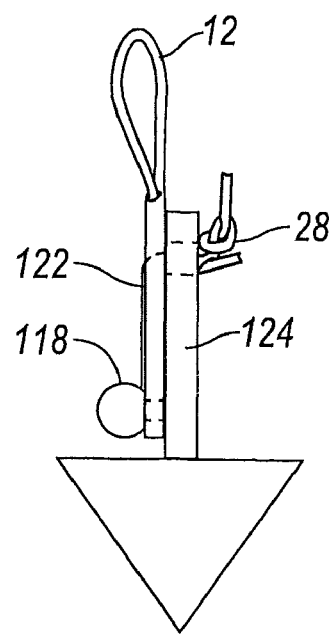

In use, the adjustable member 12 is secured to the plate tip 112 by passing the adjustable loop 12 through the suture receiving opening 120 such that the adjustable loop 12 is on a first side 122 of the panel 116 and the securing element is on the second side 124 of the panel 116. The restriction element 28 is sized to be larger than the suture receiving opening such that the flexible construct does not slip off of the panel 116. The passage 14 is then placed on the post 118. The placement of the adjustable loop 12 and the restriction element 28 are best depicted in FIGS. 14C and 14D, respectively. The panel 116 having the flexible construct 10 thereon can be used as detailed above in connection with a single fastener or multiple fastener system.

In still further embodiments, a locking member can be passed through the two adjustable loops when they are used in an interlaced or bridge formation. The method is substantially the same as the immediately above-described technique. Instead of interlacing the adjustable loops 12 with each other, the adjustable loops 12 are placed on a self-contained locking member 140 as depicted in FIGS. 13A-13C and 12A-12C. The adjustable loops can be placed on the self-contained locking member 140 prior to or after suturing the soft tissue.

To prepare the self-contained locking member 140, an adjustable loop 12 of a flexible construct is reduced by engaging the adjusting arm 16. As shown in FIG. 12B, the I-shaped locking member 41 is used as a temporary place holder and inserted into the reduced adjustable loop 12 to maintain the integrity of the adjustable loop 12 and prevent collapse of the system. Next, the adjustable loops 12', 12'', and 12''' used for the suturing are then disposed along the passage length 14 of the flexible construct 10 as shown in FIG. 12B.

The restriction element 28 is advanced in the direction of the arrow and is passed through the small opening of the adjustable loop 12. If a temporary locking member 41 place holder was employed, it can be optionally removed. The adjusting arm 16 can be further engaged or tightened to constrict the restriction element in the adjustable loop 12.

It is understood that connecting the adjustable loops 12 can be performed prior to or after suturing the tissue. The self-contained locking member 140 allows for slack to be placed in the system between the connection of the various adjustable loops 12', 12'', and 12'''.

Figure 13A:
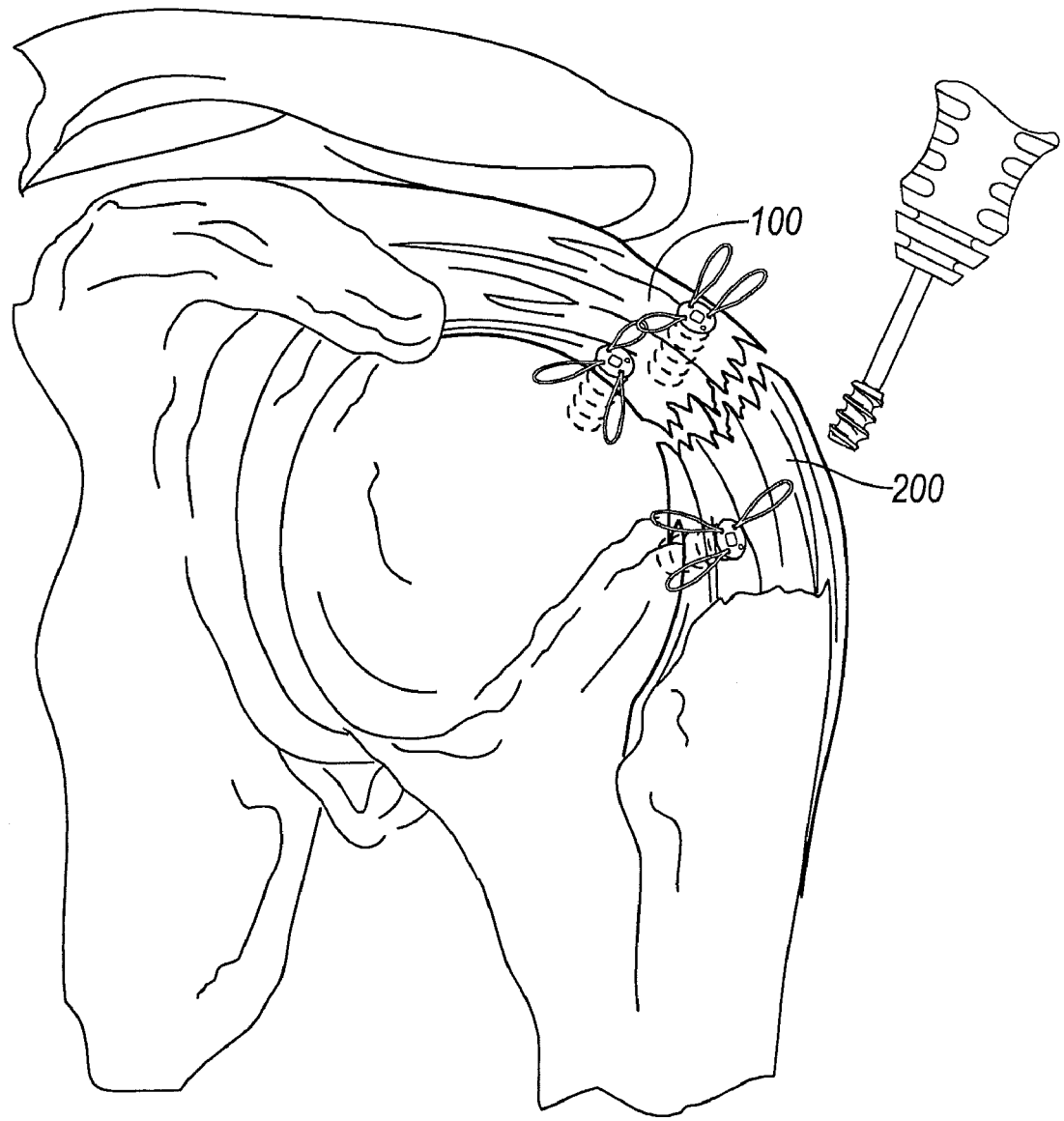
FIGS. 13A-13C depict a folded tubular flexible member pathway construct according to various embodiments.
Figure 13B:
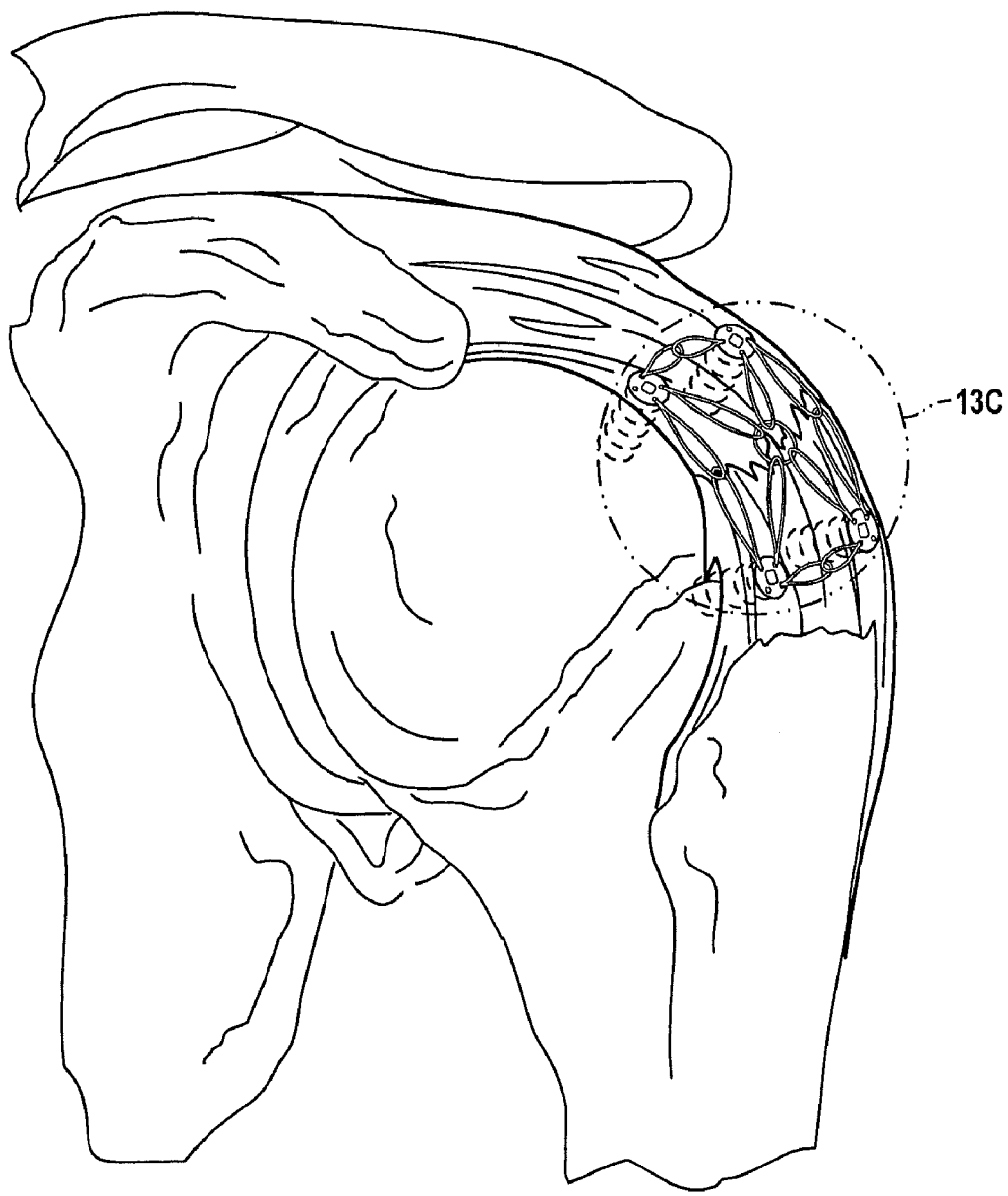
Figure 13C:
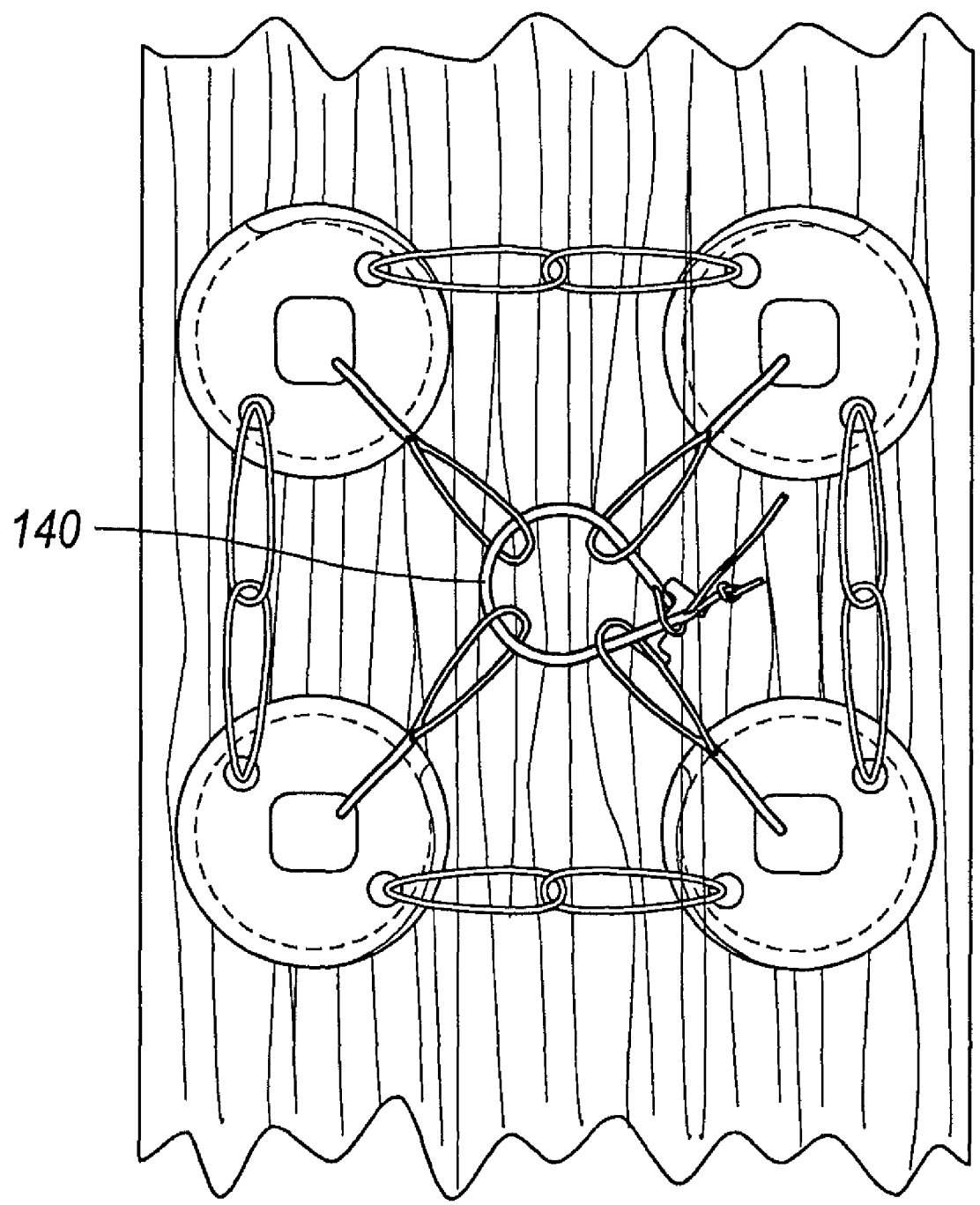

As illustrated in FIGS. 13A-13C, the self-contained locking member 140 can be strategically placed between various fasteners 92 for use in lateral row repair of a rotator cuff having torn tissue segments 150 and 152. Similar to the multi-fastener placement detailed above with respect to FIG. 11F, several fasteners 92 can be placed medially and laterally to the torn rotator cuff. The adjustable loops 12 extending from the respective fasteners can be interlaced using a combination of the interlace technique depicted in FIGS. 11G and 11H, can be interlaced by connection to the self-contained locking member 14, or a combination thereof. As shown, at least fastener 92 or row of fasteners is placed laterally with respect to the other fastener or fasteners. The self-contained locking member 140 can be placed along the length of a medial lateral row repair to facilitate increasing the footprint of the repaired tissue as shown in FIGS. 13B and 13C. It is understood that all of the multiple fastener placements disclosed herein can include the second or any subsequent fastener being placed lateral, medial, anterior, or posterior with respect to the first fastener or any other fastener.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A method of attaching a first tissue to a second tissue at a site comprising:
   a. passing at least one adjustable loop of a flexible construct through at least the first tissue, wherein the first flexible construct includes a flexible member having a body, and an end of the flexible member extends through a passage formed in the body of the flexible member to form the first flexible construct having the at least one adjustable loop;
   b. passing a locking member formed by a body of a flexible member of a second flexible construct through the at least one adjustable loop of the first flexible construct; and
   c. reducing the at least one adjustable loop of the flexible construct about the locking member such that the at least one adjustable loop is frictionally retained at the passage and locked in place by the locking member to thereby secure at least the first tissue.

2. The method of claim 1, wherein passing the locking member of the second flexible construct through the at least one adjustable loop of the second flexible construct is performed extra corporeally.

3. The method of claim 1, wherein reducing the at least one adjustable loop of the first flexible construct comprises engaging an adjusting arm defined flexible member of the first by the flexible construct.

4. The method of claim 1, further comprising selectively displacing the locking member to allow the at least one adjustable loop of the flexible construct to selectively move during the reducing of the at least one adjustable loop.

5. The method of claim 1, wherein the locking member is selected from the group consisting of a post, a knotted length of suture, a bar, a dumbbell, and an elbow.

6. The method of claim 1, further comprising pressing the locking member within, about, or adjacent to the at least one adjustable loop.

7. The method of claim 1, further comprising placing the locking member relative to the at least one adjustable loop to selectively add slack to the at least one adjustable loop.

8. The method of claim 1, further comprising passing the first and second flexible constructs through a pathway construct.

9. The method of claim 1, further comprising forming a pathway construct as a coil about the first and second flexible constructs.

10. A method of attaching a first tissue to a second tissue at a site comprising:
   a. passing at least one adjustable loop of a first adjustable flexible construct through at least the first tissue, the first flexible construct defining a first passage construct;
   b. passing at least one adjustable loop of a second adjustable flexible construct through at least the second tissue, the second flexible construct defining a second passage construct;
   c. passing a locking member through each of the at least one adjustable loops of the first and second flexible constructs; and
   d. reducing each of the at least one adjustable loops of the first and second flexible constructs about the respective locking members such that each of the at least one adjustable loops are frictionally retained at the respective passage constructs of the first and second flexible constructs and locked in place by the locking members to thereby secure at least the first tissue to the second tissue.

11. The method of claim 10, wherein reducing each of the at least one adjustable loops includes engaging an adjusting arm defined by each of the first and second flexible constructs.

12. The method of claim 10, wherein passing the at least one adjustable loop of the first and second flexible constructs through the respective first and second tissues includes positioning the first and second passage constructs between the first tissue and the second tissue.

13. The method of claim 12, further comprising substantially aligning the passage constructs of the first and second flexible constructs with each other.

14. The method of claim 12, wherein passing a locking member through each of the at least one adjustable loops includes passing a first locking member through one of the at least one adjustable loops between the first tissue and the first passage construct of the first flexible construct, and passing a second locking member through the other of the at least one adjustable loops between the second tissue and the second passage construct of the second flexible construct.

15. The method of claim 10, wherein passing a locking member through each of the at least one adjustable loops includes passing a knotted restriction element defined by each of the first and second flexible constructs through the at least one adjustable loops.

16. The method of claim 15, wherein passing a locking member through each of the at least one adjustable loops includes passing a first knotted restriction element defined by the first flexible construct through the at least one adjustable loop of the second flexible construct, and passing a second knotted restriction element defined by the second flexible construct through the at least one adjustable loop of the first flexible construct.

17. The method of claim 10, wherein the locking member includes a knotted length of suture.

18. The method of claim 10, further comprising forming a pathway construct as a coil around the first and second flexible constructs.

19. The method of claim 18, wherein forming the pathway construct as a coil around the first and second flexible constructs includes forming the pathway construct as an adjustable coil substantially around the first and second passage constructs defined by the respective first and second flexible constructs.

20. The method of claim 18, wherein forming the pathway construct as a coil around the first and second flexible constructs includes:
   a. positioning the first and second flexible constructs adjacent to each other;
   b. passing an adjusting arm defined by the first flexible construct through the at least one adjustable loop of the second flexible construct;
   c. passing the adjusting arm through the at least one adjustable loop of the first flexible construct;
   d. wrapping the adjusting arm around the first and second flexible constructs to form an adjustable coil around the first and second flexible constructs to form the pathway construct; and
   e. passing the adjusting arm through the at least one adjustable loop of the second flexible construct.

21. The method of claim 20, further comprising passing an adjusting arm defined by the second flexible construct through the at least one adjustable loop of the first flexible construct;
   wherein reducing each of the at least one adjustable loops of the first and second flexible constructs about the respective locking members includes tensioning the adjusting arms of the first and second flexible constructs.

22. A method of attaching a first tissue to a second tissue at a site comprising:
   a. passing at least one adjustable loop of a first adjustable flexible construct through at least the first tissue, the first flexible construct defining a first passage construct and including at least one first adjusting arm;
   b. passing at least one adjustable loop of a second adjustable flexible construct through at least the second tissue, the second flexible construct defining a second passage construct and including at least one second adjusting arm;
   c. positioning the first and second passage constructs between the first tissue and the second tissue;
   d. forming a pathway construct around the first and second flexible constructs by wrapping one of the first and second adjusting arms around the first and second flexible constructs to form a coil around the first and second flexible constructs;
   e. passing a locking member through each of the at least one adjustable loops of the first and second flexible constructs; and
   f. tensioning each of the at least one first and second adjusting arms thereby reducing each of the at least one adjustable loops of the first and second flexible constructs about the respective locking members such that each of the at least one adjustable loops are frictionally retained at the respective passage constructs and locked in place by the locking members to thereby secure at least the first tissue to the second tissue.

23. The method of claim 22, wherein passing a locking member through each of the at least one adjustable loops includes passing a first locking member through one of the at least one adjustable loops between the first tissue and the first passage construct of the first flexible construct, and passing a second locking member through the other of the at least one adjustable loops between the second tissue and the second passage construct of the second flexible construct.

24. The method of claim 22, wherein passing a locking member through each of the at least one adjustable loops includes passing a first knotted restriction element defined by the first flexible construct through the at least one adjustable loop of the second flexible construct, and passing a second knotted restriction element defined by the second flexible construct through the at least one adjustable loop of the first flexible construct.

25. The method of claim 22, wherein the locking member includes a knotted length of suture.

26. The method of claim 22, wherein passing a locking member through each of the at least one adjustable loops of the first and second flexible constructs includes passing a locking member through each of the at least one adjustable loops between the loops and a side of the respective soft tissue opposite a side facing the first and second passage constructs.

27. The method of claim 22, further comprising forming the coil with the at least one first adjusting arm and passing the at least one first adjusting arm through the at least one adjustable loop of the second flexible construct, and passing the at least one second adjusting arm through the at least one adjustable loop of the first flexible construct before tensioning each of the at least one first and second adjusting arms.

\* \* \* \* \*

UNITED STATES PATENT AND TRADEMARK OFFICE
CERTIFICATE OF CORRECTION

| | | |
|---|---|---|
| PATENT NO. | : 7,959,650 B2 | |
| APPLICATION NO. | : 12/196398 | |
| DATED | : June 14, 2011 | |
| INVENTOR(S) | : Ryan A. Kaiser | |

It is certified that error appears in the above-identified patent and that said Letters Patent is hereby corrected as shown below:

Column 1,
Line 8, after "U.S. Pat. No. 7,601,165" insert --;--.

Column 1,
Line 10, "to" should be --and--.

Column 2,
Line 2, "fist" should be --first--.

Column 2,
Line 13, after "first" insert --tissue--.

Column 2,
Line 16, after "first" insert --tissue--.

Column 2,
Line 62, "FIG. 9A-9C" should be --FIGS. 9A-9C--.

Column 3,
Line 14, "FIGS. 1-14C" should be --FIGS 1-14D--.

Column 5,
Line 66, "to" should be --by a--.

Column 10,
Line 66, "second" should be --first--.

Column 11,
Line 3, after "defined" insert --by the--.

Signed and Sealed this
Thirty-first Day of January, 2012

David J. Kappos
*Director of the United States Patent and Trademark Office*

Column 11,
Line 4, delete "by the" before "flexible construct".